「 
US011278184B2

(12) United States Patent
Johnsen et al.

(10) Patent No.: US 11,278,184 B2
(45) Date of Patent: Mar. 22, 2022

(54) MEDICAL SAMPLING DEVICE

(71) Applicant: AMBU A/S, Ballerup (DK)

(72) Inventors: Lasse Markworth Johnsen, Birkerod (DK); Jonas Hjortlund, Copenhagen S (DK); Martin Refslund Nielsen, Solbjærget (DK)

(73) Assignee: AMBU A/S, Ballerup (DK)

( * ) Notice: Subject to any disclaimer, the term of this patent is extended or adjusted under 35 U.S.C. 154(b) by 548 days.

(21) Appl. No.: 16/281,067

(22) Filed: Feb. 20, 2019

(65) Prior Publication Data

US 2019/0254505 A1   Aug. 22, 2019

(30) Foreign Application Priority Data

Feb. 21, 2018 (EP) ..................................... 18157810

(51) Int. Cl.
*A61B 1/00* (2006.01)
*A61B 10/00* (2006.01)
(Continued)

(52) U.S. Cl.
CPC ...... *A61B 1/00094* (2013.01); *A61B 1/00068* (2013.01); *A61B 10/0045* (2013.01);
(Continued)

(58) Field of Classification Search
CPC ............ A61B 1/00094; A61B 10/0045; A61B 10/0283; A61M 39/22
See application file for complete search history.

(56) References Cited

U.S. PATENT DOCUMENTS 2,946,348 A   7/1960 North
3,177,899 A   4/1965 Anderson et al.
(Continued)

FOREIGN PATENT DOCUMENTS

EP         1 908 391 A1    4/2008
WO    WO 2008/144515 A1    11/2008
(Continued)

OTHER PUBLICATIONS

Extended Search Report dated Sep. 11, 2018 in related EP Application No. 18157810.5.

*Primary Examiner* — Daniel L Cerioni
*Assistant Examiner* — Raymond P Dulman
(74) *Attorney, Agent, or Firm* — Faegre Drinker Biddle & Reath LLP

(57) ABSTRACT

A medical sampling device is disclosed for use with a medical device having a suction channel and a suction connector in fluid communication with said suction channel. The sampling device includes a suction inlet for connection to the suction connector, a suction outlet for connection to a vacuum source, a sampling inlet and outlet for connection to a sample container, and a valve including a valve member having first and second chambers and being rotatable between first and second positions. The first chamber in the first position establishes fluid communication between the suction inlet and the sampling inlet. The second chamber in the first position establishes fluid communication between the sampling outlet and the suction outlet. One of the first and the second chambers in the second position establish fluid communication between the suction inlet and the suction outlet.

18 Claims, 10 Drawing Sheets

(51) Int. Cl.
*A61B 10/02* (2006.01)
*A61B 10/04* (2006.01)
*A61M 39/22* (2006.01)
*A61B 1/005* (2006.01)
*A61B 1/015* (2006.01)
*A61B 1/018* (2006.01)
*A61B 1/05* (2006.01)
*A61B 1/06* (2006.01)
*A61M 1/00* (2006.01)

(52) U.S. Cl.
CPC .......... *A61B 10/0283* (2013.01); *A61B 10/04* (2013.01); *A61M 39/22* (2013.01); *A61B 1/005* (2013.01); *A61B 1/015* (2013.01); *A61B 1/018* (2013.01); *A61B 1/05* (2013.01); *A61B 1/0684* (2013.01); *A61M 1/0023* (2013.01)

(56) References Cited

U.S. PATENT DOCUMENTS

| | | | |
|---|---|---|---|
| 4,870,975 | A | 10/1989 | Cronk et al. |
| 4,909,782 | A | 3/1990 | Semm et al. |
| 4,922,902 | A | 5/1990 | Wuchinich et al. |
| 5,290,303 | A | 3/1994 | Pingleton et al. |
| 5,334,183 | A | 8/1994 | Wuchinich |
| 5,409,013 | A | 4/1995 | Clement |
| 6,110,127 | A | 8/2000 | Suzuki |
| 6,190,330 | B1 | 2/2001 | Harhen |
| 6,331,165 | B1 | 12/2001 | Turturro et al. |
| 6,375,625 | B1 | 4/2002 | French et al. |
| 6,632,182 | B1 | 10/2003 | Treat |
| 6,840,909 | B2 | 1/2005 | Gatto |
| 6,852,108 | B2 | 2/2005 | Barry et al. |
| 7,708,938 | B2 | 5/2010 | Mariotti et al. |
| 7,806,835 | B2 | 10/2010 | Hibner et al. |
| 7,921,876 | B2 | 4/2011 | Wright et al. |
| 8,382,660 | B2 | 2/2013 | Okada |
| 8,460,182 | B2 | 6/2013 | Ouyang et al. |
| 8,974,399 | B2 | 3/2015 | Teixeira et al. |
| 9,204,868 | B2 | 12/2015 | Furlong et al. |
| 9,408,593 | B2 | 8/2016 | Furlong et al. |
| 9,421,001 | B2 | 8/2016 | Speeg et al. |
| 9,486,185 | B2 | 11/2016 | Hibner |
| 9,486,186 | B2 | 11/2016 | Fiebig et al. |
| 9,498,193 | B2 | 11/2016 | Smith et al. |
| 9,538,994 | B2 | 1/2017 | Hibner et al. |
| 9,545,244 | B2 | 1/2017 | Parihar et al. |
| 9,603,587 | B2 | 3/2017 | Fiebig et al. |
| 9,737,285 | B2 | 8/2017 | Fiebig et al. |
| 2007/0179407 | A1* | 8/2007 | Gordon .............. A61B 5/15003 600/584 |
| 2007/0213632 | A1 | 9/2007 | Okazaki et al. |
| 2008/0183037 | A1 | 7/2008 | Ichikawa et al. |
| 2008/0287920 | A1* | 11/2008 | Fangrow ............... A61M 39/22 604/535 |
| 2010/0174210 | A1 | 7/2010 | Han et al. |
| 2013/0123663 | A1 | 5/2013 | Hibner et al. |
| 2013/0144186 | A1 | 6/2013 | Furlong |
| 2014/0288460 | A1 | 9/2014 | Ouyang et al. |
| 2014/0378864 | A1 | 12/2014 | Hibner |
| 2015/0209491 | A1 | 7/2015 | Cushner et al. |
| 2016/0256139 | A1 | 9/2016 | Hadley et al. |
| 2017/0274125 | A1 | 9/2017 | Minskoff et al. |

FOREIGN PATENT DOCUMENTS

| | | |
|---|---|---|
| WO | WO 2014/028366 A1 | 2/2014 |
| WO | WO 2015/031217 A1 | 3/2015 |
| WO | WO 2016/196536 A1 | 12/2016 |
| WO | WO 2017/075415 A1 | 5/2017 |
| WO | WO 2017/087411 A1 | 5/2017 |

* cited by examiner

B-B

A-A

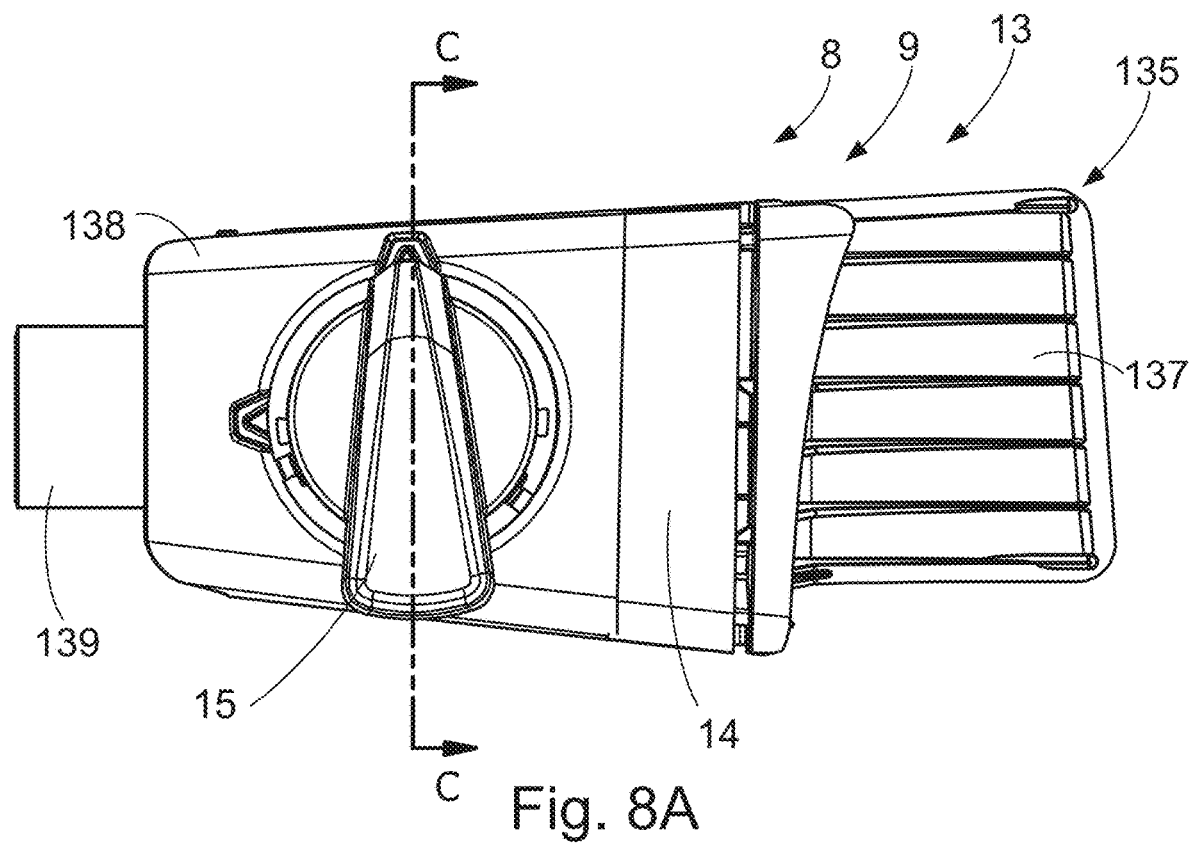
Fig. 8A
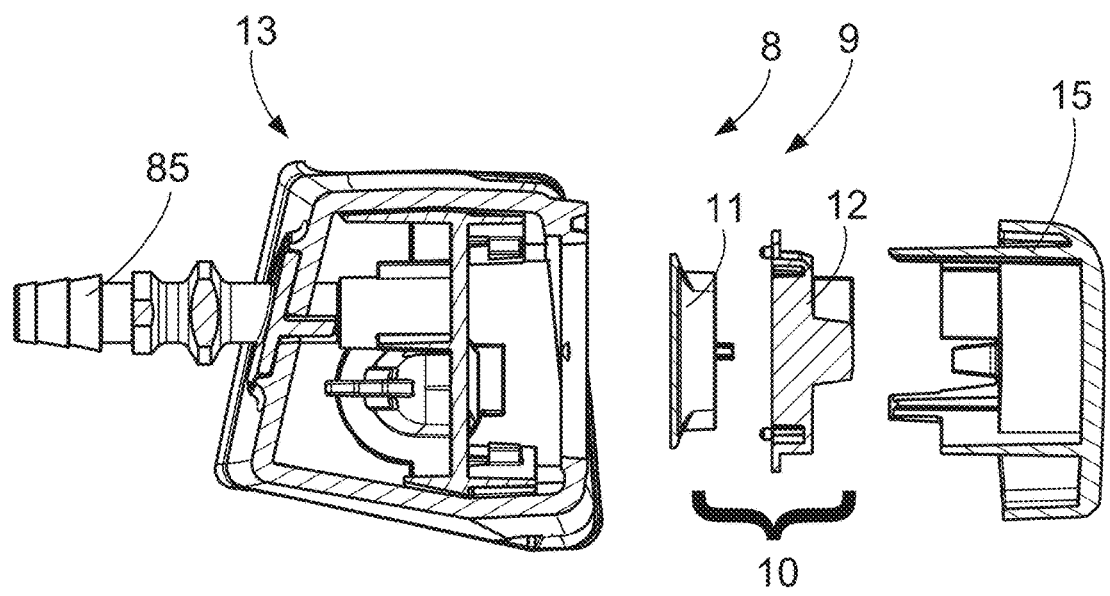
Fig. 8B    C-C

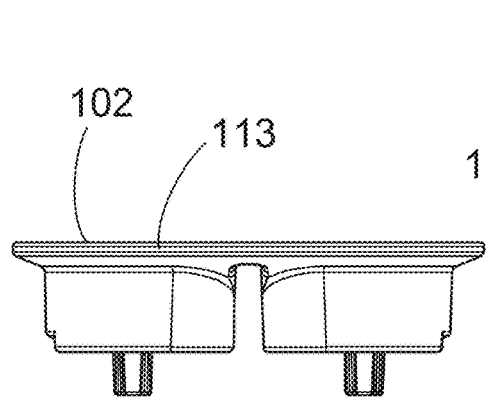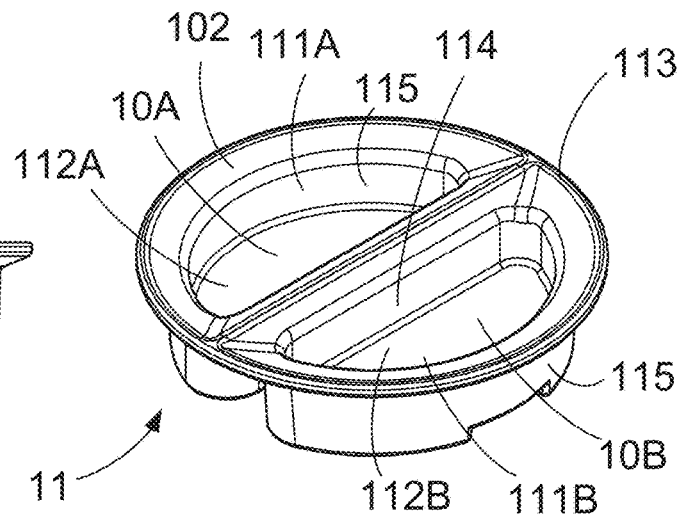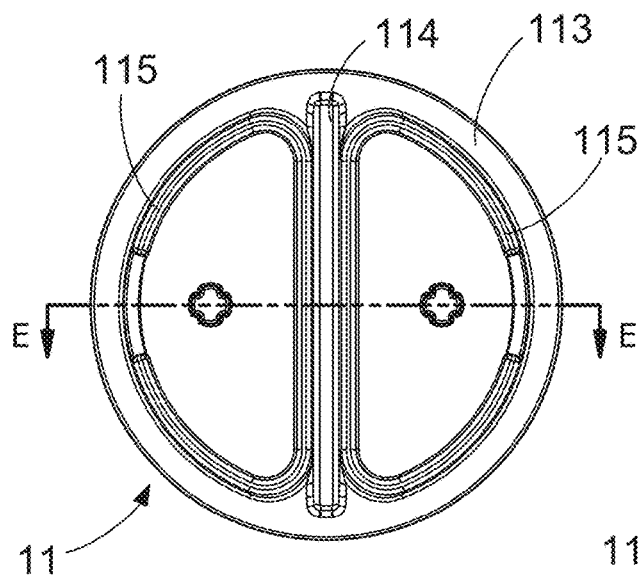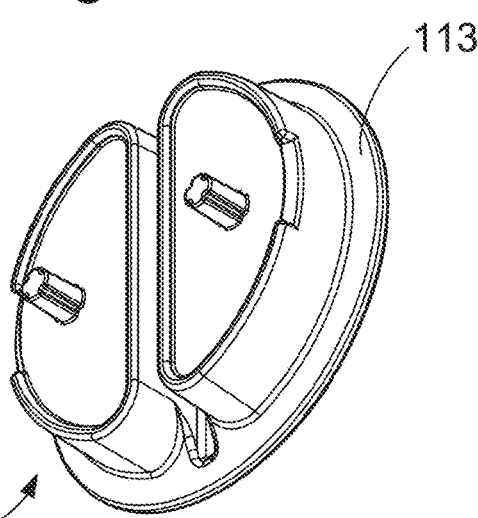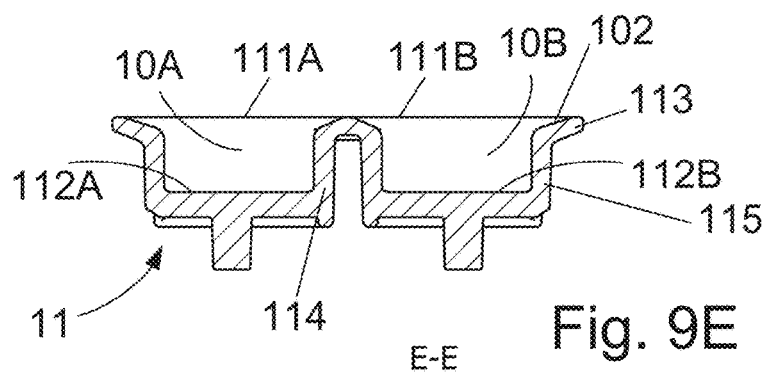

F-F

MEDICAL SAMPLING DEVICE

CROSS-REFERENCE TO RELATED APPLICATIONS

This patent application claims priority to and the benefit of European Patent App. No. 18157810.5, entitled A MEDICAL SAMPLING DEVICE, filed Feb. 21, 2018, which is incorporated by reference herein in its entirety.

TECHNICAL FIELD

The disclosure relates to a medical sampling device to be used with an medical device having a suction channel, for example a medical sampling device used with an endoscope or catherer for flushing of a body cavity and/or for sampling of bodily fluids and/or bodily tissue.

BACKGROUND

Endoscopes are well known devices for visually inspecting parts of a body of a human or animal, which may be difficult to access, such as body cavities. Typically, an endoscope comprises an elongated insertion tube with a handle at a proximal end as seen from an operator, and visual inspections means, such as a built-in camera, at a distal end of the elongated insertion tube. This definition of the terms distal and proximal, i.e. proximal being the end closest to the operator and distal being the end remote from the operator, as used herein for endoscopes in general, is adhered to in the present specification. Electrical wiring for the camera and other electronics such as LED lighting typically runs along an inside of the elongated insertion tube from the handle to the tip at the distal end. Instead of using cameras, endoscopes may also be fiber-optic, in which case the optical fibers typically run along an inside of the elongated insertion tube. A working or suction channel may run along the inside of the insertion tube from the handle to the tip, allowing liquid to be removed from the body cavity or allowing for insertion of surgical instruments or the like into the body cavity. The suction channel may be connected to a suction connector, typically positioned at a handle at the proximal end of the insertion tube.

Medical sampling devices as mentioned above are, inter alia, used in procedures such as bronchial lavage (BL), bronchial wash (BW) or bronchoalveolar lavage (BAL), which are commonly used procedures for obtaining samples of organic material from a lung segment of a patient. These may be carried out by flushing a lung segment with sterile water, usually a sterile aqueous saline solution, and then sucking the water into a sample container. More specifically, the distal end of the insertion tube of an endoscope is advanced to the location in the lung where the sample is to be taken. In bronchoalveolar lavage, the distal end is then pressed into firm engagement against the interior of the lung to help securing the position in a process commonly referred to as wedging.

Via the suction channel of the endoscope, fluid, such as sterile water, e.g. a 0.9% saline solution, or isotonic saline, is instilled into the lung at the sample location and as much as possible extracted again, now containing organic material in the form of bodily fluids and/or tissue, and thus constituting a medical sample. Typically, this is done by attaching a filled syringe of a volume between 20 ml and 60 ml, e.g. 50 ml to the suction channel of the endoscope, via a communication port in the endoscope's handle. The syringe is then used for each instillation as well as the subsequent extraction. This process is normally repeated several times in a row with new syringes, e.g. three to four, the samples being suitable for various purposes, depending which number of sample in the sequence they are, because the composition of the organic material varies. If the syringe is used for extraction, the sample would be transferred to a sample container suitable for securing biological material. Upon extraction, the sample containers are, therefore, normally labelled accordingly.

As an alternative to extraction using the syringe, the extraction may be performed in-line using an external suction and a Lukens trap, e.g. as disclosed in U.S. Pat. No. 4,643,197.

Using a Lukens trap attached to the endoscope in the manner disclosed in U.S. Pat. No. 4,643,197, i.e. interposed in the flexible suction line leading from the endoscope to the vacuum source or suction source (the two terms are used synonymously in the present specification), may involve several disadvantages when carrying out the procedure. One such disadvantage may be that the operator has only little sense of and attention to the orientation of the trap being suspended on the line since the operator's attention may be focused on other parts of the procedure, e.g. the delicate parts of the procedure within the patient. It, therefore, may happen that the Lukens trap inadvertently ends up in an orientation where the sample is lost because it gets sucked out of the trap by the suction source. Another disadvantage is that there is a lot of work involved in connecting and disconnecting tubes as well as other parts, e.g. if the operator needs to change between obtaining a sample and suction in order to clean without sampling.

U.S. Pat. No. 6,375,625 discloses an in-line specimen trap with a cap coupled to a specimen container. A rotatable member in the cap comprises through-going openings and may be rotated to provide fluid communication between inlets and outlets.

It is therefore desirable to provide an improved sampling device, and a method of using said sampling device, capable of eliminating or mitigating the shortcomings of prior sampling devices and methods of using same.

SUMMARY

On this background, it may be seen as an object of the present invention to provide a medical sampling device, which may be cheaper or easier in manufacture, may provide improved sealing properties, may provide easier or simpler operation, may improve sample-taking, and/or may reduce a risk of losing the sample. One or more of these objects may be achieved by one or more embodiments described or claimed herein.

In some embodiments, a medical sampling device is provided for use with a medical device having a suction channel and a suction connector in fluid communication with said suction channel, the medical sampling device comprising: a suction inlet adapted to be connected to the suction connector; a suction outlet adapted to be connected to a vacuum source; a sampling inlet adapted to be connected to a sample container; a sampling outlet adapted to be connected to the sample container; and a valve having a valve member and a valve housing, wherein the valve member has a first and a second chamber and is rotatable in relation to the valve housing between a first and a second position, wherein in the first position, the first chamber establishes fluid communication between the suction inlet and the sampling inlet and the second chamber establishes fluid communication between the sampling outlet and the suction outlet, and wherein in the second position, one of the first and the second chamber establishes fluid communication between the suction inlet and the suction outlet.

In a variation of the preceding embodiment, in the second position, the other of the first and the second chamber establishes fluid communication between the sampling inlet and the sampling outlet, and the valve member blocks fluid communication between the suction inlet and the sampling outlet.

In some embodiments, a method of assembly of a medical sampling device is provided, the method comprising: providing a valve member having a first chamber and a second chamber; providing a valve housing having a suction inlet, a suction outlet, a sampling outlet, a sampling inlet, and a valve member spacing; and attaching the valve member in the valve member spacing of the valve housing so as to be rotatable in relation to the valve housing between a first position and a second position, so that the first chamber in the first position establishes fluid communication between the suction inlet and the sampling inlet, the second chamber in the first position establishes fluid communication between the sampling outlet and the suction outlet, and the first chamber or the second chamber in the second position establishes fluid communication between the suction inlet and the suction outlet.

In some embodiments, a method of using the medical sampling device is provided.

In some embodiments, a medical kit is provided, the medical kit comprising the medical sampling device described above as well as an endoscope or a catheter adapted for attachment to said sampling device and/or a sample container adapted for attachment to said sampling device.

In some embodiments, a medical system is provided, the medical system comprising: an endoscope or a catheter having a suction channel and a suction connector in communication with said suction channel, the medical sampling device described above, attached to the endoscope or catheter, and a sample container attached to the medical sampling device. A method of assembly of the medical system is also provided.

DESCRIPTION

A first aspect of the invention involves a medical sampling device for use with a medical device having a suction channel and a suction connector in fluid communication with said suction channel, the medical sampling device including a suction inlet for connection to the suction connector, a suction outlet for connection to a vacuum source, a sampling outlet for connection to a sample container, a sampling inlet for connection to the sample container, and a valve having a valve member and a valve housing, wherein the valve member has a first and a second chamber and is rotatable in relation to the valve housing between a first and a second position, the first chamber in the first position establishing fluid communication between the suction inlet and the sampling inlet, the second chamber in the first position establishing fluid communication between the sampling outlet and the suction outlet, and one of the first and the second chamber in the second position establishing fluid communication between the suction inlet and the suction outlet. Example medical devices include an endoscope, a catheter, and other devices operable for flushing of a body cavity and/or for sampling of bodily fluids and/or bodily tissue.

Advantages associated with the medical sampling device disclosed herein may include one or more of the following:

The medical sampling device may effectively provide a sampling mode in the first position and a shunt or bypass mode in the second position. In the sampling mode, fluid may flow from the suction inlet to the sampling inlet, potentially into a connected sample container, on to the sampling outlet, and on to the suction outlet. In the shunt or bypass mode, fluid may flow from the suction inlet to the suction outlet, bypassing the sampling inlet and sampling outlet. Hereby, it is possible to sample in the first position and to bypass the sampling in the second position. For example, the first position may be used for sampling, the second position being used for flushing only. The medical sampling device may be configured so that the valve and the device itself are effectively sealed to be fluid-tight in relation to the surroundings and/or so that fluid flow between the respective inlets and outlets is efficiently and effectively provided and/or so that any other fluid flow through the medical sampling device is avoided in the first and second positions, respectively. The medical sampling device may be manufactured from low-cost materials, such as plastic materials. Furthermore, it may be configured to be readily assembled in a low-cost procedure. For these reasons and others, the medical sampling device may be configured for single-use purpose and/or for use with single-use endoscopes or catheters. The valve housing may include several or all of the stationary parts of the medical sampling device, including fluid channels extending through the device, allowing for these parts to be integrally formed and/or moulded and/or cast, cost and assembly advantages being associated therewith. The valve may be configured so that vacuum pressure exerted on the suction outlet improves fluid tightness of the valve as explained further below. The medical sampling device may be configured so that no fluid flow will occur through the medical sampling device when the valve is in the second position and no sample container is connected to the medical sampling device, in particular when the sampling inlets and outlets are not connected by a sample container, i.e. so that no fluid communication is established between the sampling inlets and outlets. The valve may be configured so that low friction is provided between the valve member and the valve housing, especially in an operating state where a vacuum pressure is applied to the suction outlet.

In some embodiments, the valve member may in the first and second positions, respectively, substantially block all other fluid communication between the inlets and outlets of the medical sampling device. Thus, the valve member may in the first position block fluid communication between a first and a second pair of inlets and outlets, the first pair being the suction inlet and the sampling inlet, the second pair being the sampling outlet and the suction outlet. Correspondingly, the valve member may in the second position block fluid communication between a third and a fourth pair of inlets and outlets, the third pair being the suction inlet and the suction outlet, the fourth pair being the sampling outlet and the sampling inlet.

In the second position, the first or the second chamber establishes fluid communication between the suction inlet and the suction outlet. Which of the chambers that establishes the fluid communication in the second position may depend on which way the valve member is rotated, and with how many degrees, in order to rotate the valve member from its first to its second position, and reversely. For example, in some embodiments, the medical sampling device is configured so that when the valve member is rotated about 90° clockwise from the first position, the valve member assumes its second position, the second chamber establishing the fluid communication between the suction inlet and the suction outlet. Alternatively, the valve member may be rotated about 90° counter-clockwise from its first position, whereby the first chamber establishes the fluid communication between the suction inlet and the suction outlet in the second position. Correspondingly, the valve member may be configured to be rotated, e.g. 70 to 110° or 80 to 100° or about 90°, either clockwise or counter-clockwise when rotating from the first to the second position and be rotated with a similar angle counter-clockwise or clockwise, respectively, i.e. in the opposite direction, when rotating from the second to the first position.

One or more valve member stopping elements may be provided to limit the rotational movement of the valve member, e.g. configured so that when having rotated from the first to the second position, the valve member is not allowed to rotate further in that direction, and/or when having rotated from the second to the first position, the valve member is not allowed to rotate further in that direction.

The valve member may be substantially disc-shaped and/or have a substantially round, cylindrical and/or circular-cylindrical shape. The valve member may comprise a potentially fluid-tight wall separating the two chambers from each other. The first and/or second chamber may each be substantially cylindrical, potentially with cylinder side surfaces extending substantially in a direction parallel to an axial direction defined by an axis about which the valve member is rotatable, and/or may be substantially crescent-shaped, rectangular or triangular in shape, potentially in a cross-section normal to a rotation axis of the valve member. The above-mentioned valve member wall may separate the two chambers from each other, potentially so as to block fluid communication between the two chambers. This wall may be linear in a cross-section perpendicular to a rotation axis of the valve member, potentially providing linear sides of the crescent shape if the chambers are crescent-shaped. Respective rounded or semi-circular walls may then form the rounded parts of the crescent shapes. These walls may form part of a circumferential wall of the valve member extending potentially along a cylinder side surface in the axial direction.

The valve housing may be a stationary part of the medical sampling device in relation to which the valve member is rotatable. This stationary part may be held stationary in relation to the endoscope or a handle thereof when the medical sampling device is fixated to the endoscope.

The valve housing may be provided as one, potentially integral, and/or integrally moulded part or may comprise several parts fixated and/or attached to each other to provide the valve housing. The valve housing may comprise a valve housing part, which may include and/or house the suction inlet and/or a channel for connecting the suction inlet to the suction connector and/or the suction outlet and/or a channel for connecting the suction outlet to the vacuum source and/or the sampling outlet and/or a channel for connecting the sampling outlet to the sample container and/or a sliding spacing for a slideable locking member as described further below and/or a flange or latch member as described further below and/or a valve member spacing in which the valve member may be positioned. Any one or more of these may be integral and/or integrally moulded with the valve housing. The valve housing may also comprise a valve housing shell which may potentially be positioned to surround and/or encircle and/or house the valve housing part or any one or more parts of the valve housing part and/or may form one or more outer surfaces of the valve housing. During assembly of the medical sampling device, provision of the valve housing shell separately from the valve housing part may provide the advantage that the valve member may initially be positioned in a valve member spacing of the valve housing after which the valve housing shell may be positioned to at least partially cover the valve member and/or to hold the valve member in position and/or to cover parts of, or all of, the valve housing part. The valve housing shell may be snappable and/or snapped onto the valve housing part, potentially in an irreversible manner.

The valve housing or the valve housing part may comprise a seal surface, the valve member comprising a corresponding seal surface, the seal surfaces abutting each other and sealing the chambers and interior parts of the valve, in which fluid flows, such as channels and valve ports, from the surroundings. The seal surfaces may be provided on one or more gasket members, see also below. The seal surfaces may be provided to extend along a peripheral edge of the valve member and/or along a wall separating the two chambers.

The valve housing may comprise the suction inlet and/or the suction outlet and/or the sampling outlet, and/or the sampling inlet. The suction inlet and/or the suction outlet and/or the sampling outlet, and/or the sampling inlet may be provided at a surface of the valve housing and/or of the medical sampling device. Any one or more of these inlets and outlets may be provided as fluid ports of the medical sampling device, potentially of the valve housing, the valve housing part or the valve housing shell. The suction inlet may be positioned at a distance in a radial direction from a rotation axis of the valve member and from the valve member or in a direction parallel to such a radial direction, potentially so that an insertion direction of a suction connector of the endoscope is aligned with said direction. Similarly, the sampling inlet and outlet may be positioned a distance in a radial direction from said rotation axis of the valve member and from the valve member or in a direction parallel to such a radial direction, potentially so that an insertion direction of a sampling connector of the medical sampling device and/or of a sample container is aligned with said direction, where such a sampling connector may comprise one of or both the sampling inlet and sampling outlet. The suction outlet may be positioned a distance from the valve member in an axial direction of said rotation axis of the valve member or in a direction parallel to such an axial direction, potentially so that an insertion direction of a suction connector of the medical sampling device or a suction source tube is aligned with said direction. One or more of these positions may allow for the medical sampling device to be configured so that connection of an endoscope and/or a sample container and/or a suction source to the respective inlets and outlets of the medical sampling device is made easy and advantageous for operation of the medical sampling device and/or a medical system comprising the medical sampling device and/or endoscope and/or sample container and/or suction source.

The medical sampling device, specifically the valve housing, may comprise a number of internal fluid channels or conduits allowing for fluid flow through the medical sampling device and connecting the inlets and outlets to valve ports of the valve, the valve ports establishing fluid communication between the respective channels and the first and/or second chambers, depending on the rotary position of the valve member as described above. These channels may be provided to be fluid tight in relation to each other and/or be provided in the valve housing. Thus, a first suction channel may connect the suction inlet to a first valve port, and/or a first sampling channel may connect the sampling inlet to a second valve port, and/or a second sampling channel may connect the sampling outlet to a third valve port, and/or a second suction channel may connect the suction outlet to a fourth valve port. The first to fourth valve ports may be configured so as to be distributed in a sequence first to fourth in a clockwise circumferential direction about a rotation axis of the valve member. In the first position of the valve member, one or more openings of the first chamber may be aligned with the first and second valve ports, and/or one or more openings of the second chamber may be aligned with the third and fourth valve ports. In the second position of the valve member, one or more openings of the first chamber may be aligned with the first and fourth valve ports, and/or one or more openings of the second chamber may be aligned with the second and third valve ports, or, alternatively, one or more openings of the second chamber may be aligned with the first and fourth valve ports, and/or one or more openings of the first chamber may be aligned with the second and third valve ports. The openings of the first and second chambers may respectively comprise at least one top opening providing said fluid communication between the respective inlets and outlets in the first and second positions of the valve member via the respective first and second chambers, a bottom surface positioned oppositely from the top opening, and lateral surfaces surrounding and connected to the bottom surface, the bottom and lateral surfaces establishing potentially fluid-tight internal surfaces of the respective chamber. This top opening may alternatively be provided as two or more top openings of one or each chamber.

One or more of the first, second, third and fourth valve ports may be provided in a substantially plane surface of the valve housing or the valve housing part. This plane surface may extend substantially in a plane extending in radial directions in relation to a rotation axis of the valve member. Hereby, the valve ports may be configured to be suitably aligned with respective openings, which may be the top openings as discussed above, of each of the first and second chambers. A seal surface of the valve housing, as is discussed further below, may be provided as parts of this plane surface and may surround all four valve ports.

One or more of the channels may comprise a bent section, potentially of approximately 90 degrees, allowing the channel to extend from the respective valve port and to the respective inlet or outlet when the respective inlet or outlet is a termination of a channel section extending in a direction at an angle, such as a right angle, to an axis of rotation of the valve member. The suction inlet and/or sampling inlet and/or sampling outlet, and/or suction outlet may form terminations, i.e. where the respective channel ends, of the first suction channel, the first sampling channel, the second sampling channel, and the second suction channel, respectively. Similarly, the above described valve ports may form respective terminations of and at the other end of the respective channel. When the medical sampling device is configured according to this, the channel section leading to the suction inlet and the channel sections leading to the first and second sampling outlets may extend in a direction at an angle, such as a substantially right angle, to an axis of rotation of the valve member, whereas the channel section leading to the suction outlet may extend in a direction substantially parallel to an axis of rotation of the valve member. This may allow for easy attachment to the endoscope, sample container and vacuum source.

A rotary knob, potentially rotatable by hand, may be attached to be rotationally fixed to and/or provided integrally with the valve member or a part thereof. During assembly of the medical sampling device, the rotary knob may be attached to or snapped to the valve housing, the valve housing part, the valve housing shell and/or the valve member so as to be rotatable in relation to the valve housing. For instance, the valve housing, the valve housing part and/or the valve housing shell may comprise one or more holding elements engaging one or more corresponding holding elements of the rotary knob when the rotary knob is attached to form part of the medical sampling device. One or more of these holding elements or these corresponding holding elements may be configured as barbs and/or to provide a snap lock of the rotary knob when the rotary knob is attached to form part of the medical sampling device. For example, the rotary knob may comprise a partly or wholly circumferential edge, which may be beveled or chamfered and may force one or more legs, which may be provided as part of the valve housing, the valve housing part, the valve housing shell, and/or the valve member, and which may have a barb extending outwardly or inwardly in relation to the valve member when the rotary knob is pushed into position, so that the leg may be pushed outwardly or inwardly and, after positioning of the rotary knob, may snap back so that the barb snaps into engagement with the circumferential edge. Alternatively, the circumferential edge may be provided on the valve housing, the valve housing part, the valve housing shell, and/or the valve member, and the one or more legs may be provided as part of the rotary knob, thus achieving the same effect.

The sampling device may generally be adapted for single use. Accordingly, the sampling device may be constructed from low cost materials, such as plastics because it need not be able to withstand the harsh circumstances of cleaning and sterilization, such as the high temperatures of an autoclave.

The suction inlet may be or comprise a female connector or socket or a male connector or tube connector defining an insertion direction adapted to receive the suction connector of the endoscope in said insertion direction, potentially for forming a fixed connection as described further below, and the sampling device may, furthermore, be adapted to engage the endoscope in a manner preventing rotation around the suction connector. Thereby, a good sense of orientation may be maintained at all angles.

The medical sampling device may be configured to engage the endoscope in a manner preventing rotation around the suction connector.

The sampling inlet may be or comprise a sample container connector adapted for connection to a sample container. This may allow the sample container to be easily attached, removed, and/or replaced during a sampling procedure. The sample container connector may extend in a direction parallel to or coincident with said insertion direction.

The medical sampling device may be used for flushing one or more body parts, such as lungs, for sampling bodily fluids, and/or for sampling tissue parts, potentially tissue parts cut by an instrument applied through the suction channel of the endoscope. Such tissue parts are usually removed with the endoscope, but may also be removed by flushing by use of the medical sampling device according to the invention. The design of the sample container may be configured differently, depending on whether tissue is to be separated from a liquid or liquid is to be separated from air.

The medical sampling device may be suitable for or used in bronchial lavage (BL), bronchial wash (BW) or bronchoalveolar lavage (BAL).

The term "endoscope" may be defined as a device suitable for insertion into and examination of natural and/or artificial body openings, e.g. for exploration or flushing or for sampling of bodily fluids or bodily tissue in a bodily cavity, such as a lung cavity.

The term "catheter" may be defined as a device suitable for being inserted into natural and/or artificial body openings, e.g. for flushing or for sampling of bodily fluids or bodily tissue.

Additionally, or alternatively, the terms "endoscope" and the term "catheter" may, respectively, be denoted "a medical device".

As used in the present specification, the term "establishing fluid communication between two openings", such an "opening" potentially being an inlet or an outlet, may be defined as a fluid being allowed to flow between two fluid openings. An alternative wording of the term may be "establishing a fluid connection between two openings". An alternative wording of the term "establishing" in this context may be "providing".

In an embodiment according to the first aspect of the invention, the medical sampling device is configured so that when a vacuum pressure from the vacuum source is exerted on the second chamber in the first position and on the first or second chamber in the second position, the vacuum pressure pulls at least a part of the valve member towards the suction outlet.

In another embodiment, the valve member comprises an exterior part and an interior part, and the interior part is potentially a gasket member provided separately from and movably attached to the exterior part so as to potentially be movable in relation to, in an axial direction of, the valve member, the gasket member potentially laterally surrounding the first and/or the second chamber so that when a vacuum pressure is exerted on the suction outlet in the first and/or the second position, the vacuum pressure potentially causes the gasket member to move in the direction towards the suction outlet.

The gasket member may be moveable as described by being slideable.

The interior member may be rotationally fixed to the exterior part so that both members rotate when the valve member is rotated.

The gasket member may in the first position of the valve member surround the first and second valve ports and/or the first chamber. The valve member may comprise a further gasket member which in the first position surrounds the third and fourth valve ports mentioned above and in the second position potentially surrounds the second and third valve ports or the first and fourth valve ports mentioned above.

The gasket member may surround the first to fourth valve ports mentioned above and/or surround the first and second chambers.

The gasket member may be provided as two separate gasket member parts, each gasket member part potentially surrounding a respective one of the first and second chambers. A first of the gasket member parts may in the first position of the valve member surround the first and second valve ports mentioned above and in the second position surround the third and fourth valve ports or the first and fourth valve ports. Correspondingly, a second gasket member part may in the first position of the valve member surround the third and fourth valve ports and in the second position surround the first and fourth valve ports or the second and fourth valve ports.

Alternatively, the gasket member may be provided as one, integral gasket member, which surrounds the first chamber and surrounds the second chamber, and/or which may extend to separate the first and second chambers from each other, in which case, the gasket member may include a wall separating the first and second chambers.

A rotary knob as described above may be attached to be rotationally fixed to or provided integrally with the exterior part.

Any one or more or all parts of the valve housing and the exterior part may generally be manufactured from the same material.

Alternatively, or additionally, the gasket member may be manufactured from, essentially consist of or comprise a thermoplastic polymer or an elastomer, such as a thermoplastic elastomer, such as silicone or silicone rubber.

Any one or more or all parts of the valve housing and the exterior part may generally be manufactured from, essentially consist of or comprise a material having a shore A hardness above 90 or a shore D hardness above 75 or 100, measured according to standard ASTM D2240.

Any one or more or all parts of the valve housing and the exterior part may generally be manufactured from, essentially consist of or comprise a thermoplastic polymer or an elastomer, such as a thermoplastic elastomer, such as polyoxymethylene (POM) and/or a methylmethacrylate acrylonitrile butadiene styrene (MABS).

The gasket member may be manufactured of, essentially consist of or comprise a TPE, which may be medical grade and/or low-friction, such as KRAIBURG® TPE, MC/LF Series, tradename TERMOLAST® M, specifically one of type TM7LFT, TM6LFT, TM5LFT, TM4LFT, TM3LFT (datasheet of 27 May 2014). A low-friction TPE may reduce torsion when turning a rotary knob in operation of the medical sampling device. TPE has been shown to generally provide advantageous friction characteristics and to be suitable for being used together with MABS or POM as mentioned above.

Alternatively, or additionally, the gasket member material may be of a material with a shore A value of 10 to 100, 20 to 100, 30 to 100, 40 to 90, 50 to 90, 60 to 80 or 65 to 75, measured according to standard ASTM D2240 or DIN ISO 7619. A shore A value around 70 has been shown to provide a good compromise between the hardness of the material and manufacture by means of injection moulding of the gasket member.

Alternatively, or additionally, the gasket member material may be of a material with a tensile strength measured according to standard DIN 53504/ISO 37 of 3 to 20, 5 to 18, 7 to 14, 9 to 14, 10 to 13 or 11 to 13 MPa.

Alternatively, or additionally, the gasket member material may be of a material with a compression set 72 h/RT measured according to DIN ISO 815 of 10 to 50, 20 to 40, 25 to 35 or 28 to 32%. A lower compression set may affect a pressure tension of the gasket member over time.

Alternatively, or additionally, any one or more or all parts of the valve housing and the exterior part and/or gasket member may be injection moulded. A higher shore A hardness may be of advantage in injection moulding of the gasket member.

Alternatively, or additionally, any one or more or all parts of the valve housing and the exterior part may be injection moulded.

Alternatively, or additionally, any one or more or all parts of the valve housing and the exterior part may be of material having a higher shore A value than the gasket member.

In a development of the present embodiment, each of the first and second chambers comprises at least one top opening providing said fluid communication between the respective inlets and outlets in the first and second positions of the valve member via the respective first and second chambers, a bottom surface positioned oppositely from the top opening, and lateral surfaces surrounding and connected to the bottom surface, the bottom and lateral surfaces establishing internal surfaces of the respective chamber, and wherein the lateral surfaces and/or the bottom surface are provided as parts of the gasket member.

In another or further development of the present embodiment, the gasket member comprises a lip extending at least partly between and/or being compressed between the exterior part and a seal surface of the valve housing.

Such a lip may improve sealing and may reduce friction between the valve member and the seal surface of the valve housing.

The lip may extend in an entire circumference of an opening, such as the top opening described above, into the first and/or second chamber.

The lip may extend from a lateral wall of the gasket member, outwardly and/or inwardly, potentially in a radial direction defined in relation to an axial direction of a rotation axis of the valve member. This may further improve sealing and/or reduce friction.

In another embodiment, the valve member is rotatable about an axis defining an axial direction, and a first valve port connected to the suction inlet and/or a second valve port connected to the sampling outlet and/or a third valve port connected to the suction outlet and/or a fourth valve port connected to the sampling inlet is/are provided in a valve housing surface extending substantially radially in relation to the axial direction.

Each of the first and second chambers may, as described above, comprise at least one top opening providing said fluid communication between the respective inlets and outlets in the first and second positions of the valve member as described above via the respective first and second chambers. In the present embodiment, this top opening may be suitably aligned with the relevant valve ports in the first and second positions of the valve member.

In another embodiment, the medical sampling device is configured to be fixated to the endoscope when connected to the suction connector thereof.

Another aspect of the invention involves a medical sampling device for use with a medical device for sampling of bodily fluids, the medical device having a suction channel and a suction connector in communication with said suction channel, the medical sampling device comprising: a suction inlet for connection to the suction connector, and a suction outlet for connection to a vacuum source, wherein the medical sampling device is configured to be fixated to the endoscope when connected to the suction connector thereof.

The developments described in the following relate both to the present embodiment of the first aspect of the invention and the another aspect.

Thus, in both the present embodiment of the first aspect and said another aspect of the invention, the medical sampling device is configured so that the valve housing may be fixated to the medical device, specifically a handle of the medical device. Fixation to the medical may link and/or match an orientation of the sampling device to that of the medical device. This, in turn, may provide an operator of the medical device with a more immediate and instinctive sense of the orientation of the medical sampling device because the orientation follows that of the medical, on the handle of which the operator typically has a firm grip. As mentioned previously, an endoscope is an example medical device. Accordingly, the medical sampling device is configured so that the valve housing may be fixated to the handle of the endoscope.

The sampling device may furthermore be configured to be fixated to the endoscope in a manner preventing rotation around the suction connector.

The suction connector may be so strong and so strongly attached to the endoscope that when the medical sampling device is fixated to the endoscope, a suitably strong connection between the two is achieved. In case it is desired to provide a stronger attachment between the two, the sampling device may comprise one or more flange or latch members configured to match a shape or outer surfaces of the endoscope, specifically a handle thereof. In the fixated position of the medical sampling device, the flange member(s) may be configured to extend around at least part of a handle of the endoscope, inner surfaces of the flange member(s) potentially abutting outer surfaces of the handle. The flange member(s) may be of a relatively rigid material, such as a hard plastics material, e.g. of the same material as the remaining parts of the valve housing, and potentially with suitable flexibility and resiliency to be able to snap into engagement with the handle of the endoscope and potentially further ensure the fixation of the sampling device against movement with respect to the handle of the endoscope. Hereby, the medical sampling device may follow the movements of the endoscope handle. Since an endoscope operator is often used to gripping the handle of the endoscope and is often familiar with the orientation thereof, a risk of the endoscope ending up in an undesired orientation, e.g. where a sample in the sample container is lost, may be reduced.

In a development of the present embodiment, the medical sampling device is adapted to be fixated to the endoscope when connected to the suction connector thereof by means of a moveable locking member.

In both the present embodiment of the first aspect and said another aspect of the invention, the medical sampling device may, thus, be adapted to be fixated to the endoscope when connected to the suction connector thereof by means of a moveable locking member.

The moveable locking member may be a slideable locking member of the medical sampling device provided to be slideable in and/or in relation to the valve housing between a locked position, in which the medical sampling device is fixated to the endoscope, and an unlocked position, in which the sampling device can be positioned to be fixated to and/or be released from the endoscope.

As mentioned above, the valve housing may comprise a male or female connector or socket defining an insertion direction adapted to engage, respectively, a female or a male suction connector of the endoscope in said insertion direction, such as a standard suction connector of the endoscope. The female or male suction connector may be of the type comprising one or more circumferentially extending barbs for engaging and maintaining connection to a tube.

The moveable locking member may be configured to engage one or more such circumferentially extending barbs of a suction connector, potentially as a snap connection. In the case of a slideable locking member, the locking member may comprise one or more, such as two, locking supports that are slideable into engagement with one or more circumferentially extending barbs of a suction connector, especially when the suction connector is inserted into a socket of the valve housing. The slideable locking member may comprise a cut-out allowing for sliding of the locking member into the locked position, wherein the suction connector may extend through the cut-out in said locked position of the locking member. In this case, the locking support may be a projection extending into or towards the cut-out so that the projection is slid into the locked position of the locking member by being slid to a position abutting a barb of the suction connector after insertion of the suction connector into the socket of the valve housing.

The slideable locking member may be provided separately from or as a separate part of the valve housing and may potentially be attached to be slideable in relation to the valve housing or the remaining parts of the valve housing, but potentially not detachable from the valve housing. This may be achieved by a holding member, such as a barb, provided as part of the slideable locking member, the holding member engaging a corresponding holding member, such as a barb, of the valve housing when in the unlocked position so that the slideable locking member is prevented from being removed from the valve housing when in the unlocked position.

The slideable locking member may comprise an engagement part, which in the released position potentially extends out of the valve housing, potentially making it possible to slide the slideable locking member between the locked and released positions by engaging the engagement part and sliding the locking member, e.g. by means of a hand pushing or pulling the slideable locking member. The engagement part may be positioned to be provided substantially inside the valve housing or a valve housing shell of the valve housing when the slideable locking member is in the locked position, potentially so that an outer surface of the slideable locking member, potentially of the engagement part, is substantially flush with an outer surface of the valve housing. The slideable locking member or the engagement part may comprise a grabbing projection, potentially extending beyond the outer surface of the valve housing or the valve housing shell, the grabbing projection allowing for grabbing the slideable locking member, e.g. by means of a finger, potentially to pull the slideable locking member towards the released position so that the slideable locking member or the engagement part may be grabbed by a hand and slid the remaining distance to enter the released position.

In an alternative, or in addition, to the moveable locking member being slideable, the moveable locking member may include a moveable snap locking member allowing the valve housing to be snapped into fixation to the endoscope or a handle thereof. This may be achieved by means of one or more snapping barbs, potentially provided on flexible legs, so that the legs or barbs flexingly allow for insertion of the suction connector, the barbs potentially snapping into engagement with one or more circumferentially extending barbs thereof.

In an alternative, or in addition, to the moveable locking member being slideable, the moveable locking member may be hinged to the valve housing so as to be rotatable in relation to the valve housing. Furthermore, the moveable locking member may be rotatable in and/or in relation to the valve housing between a locked position, in which the medical sampling device is fixated to the endoscope, and an unlocked position, in which the sampling device can be positioned to be fixated to and/or be released from the endoscope.

The rotatable locking member may similarly be configured to engage one or more circumferentially extending barbs of a suction connector and may comprise a locking support that may be rotated into engagement with one or more circumferentially extending barbs of a suction connector, especially when the suction connector is inserted into a socket of the valve housing. The rotatable locking member may similarly comprise a cut-out allowing for sliding of the locking member into the locked position, wherein the suction connector may extend through the cut-out in said locked position of the locking member. And similarly, the locking support may be a projection extending into the cut-out so that the projection is slid into the locked position of the locking member by being slid to a position abutting a barb of the suction connector after insertion of the suction connector into the socket of the valve housing.

The rotatable locking member may similarly be provided as a part separate from the valve housing and may potentially be attached to the valve housing via the hinge. The rotatable locking member may comprise an engagement part similar to the engagement part of the slideable locking member as described above.

A second aspect of the invention involves a method of assembly of a medical sampling device according to any one of the above embodiments, the method comprising: providing a valve member having a first and a second chamber; providing a valve housing having a suction inlet, suction outlet, sampling outlet, and sampling inlet; and attaching the valve member in a valve member spacing of the valve housing so as to be rotatable in relation to the valve housing between a first and a second position, so that the first chamber in the first position establishes fluid communication between the suction inlet and the sampling inlet, the second chamber in the first position establishes fluid communication between the sampling outlet and the suction outlet, and the first chamber or second chamber in the second position establishes fluid communication between the suction inlet and the suction outlet.

The method may further comprise: providing an exterior part and an interior part of the valve member, the interior part being a gasket member; and positioning the gasket member so as to be slidably attached to the exterior part so as to be slidable in an axial direction of the valve member.

The interior part or gasket member may be according to any one of the embodiments of the interior part or gasket member described above.

An embodiment of the present aspect of the invention comprises attaching a rotary knob to the valve housing so that the valve member may be rotated between the first and second positions by means of rotation of the rotary knob.

The rotary knob may be positioned to be rotatable about a rotation axis of the valve member.

The rotary knob may comprise legs that engage openings or slots of the valve member, potentially positioned along a periphery of the valve member, allowing the rotary knob to rotate the valve member on rotation of the rotary knob.

The rotary knob may be according to any one of the embodiments of the rotary knob described above.

A third aspect of the invention involves a use of a medical sampling device according to any one of the above embodiments for sampling of bodily fluids and/or bodily tissue.

A fourth aspect of the invention involves a use of a medical sampling device according to any one of the above embodiments for connection with or attachment to an endoscope for flushing and/or for sampling of bodily fluids and/or bodily tissue and/or for connection with or attachment to a sample container.

A fifth aspect of the invention involves a medical kit comprising a medical sampling device according to any one of the above embodiments as well as a medical device adapted for attachment to said medical sampling device and/or a sample container adapted for attachment to said medical sampling device.

A sixth aspect of the invention involves a medical system comprising: a medical device having a suction channel and a suction connector in communication with said suction channel, a medical sampling device according to any one of the above embodiments attached to the medical device, and a sample container attached to the medical sampling device.

A seventh aspect of the invention involves a method of assembly of a medical system according to the sixth aspect of the invention, comprising: providing a medical device having a handle, a suction channel and a suction connector in communication with said suction channel, providing a medical sampling device according to an embodiment disclosed herein, providing a sample container, providing a vacuum source, connecting the suction connector to the suction inlet of the medical sampling device, attaching or fixating the medical sampling device to the handle, connecting the suction outlet of the medical sampling device to the vacuum source, and connecting the sampling inlet and sampling outlet of the medical sampling device to the sample container.

A person skilled in the art will appreciate that any one or more of the above aspects of the invention and embodiments thereof may be combined with any one or more of the other aspects of the invention and embodiments thereof.

BRIEF DESCRIPTION OF THE DRAWINGS

In the following, embodiments of the invention will be described in more detail with reference to the drawings, in which:

FIG. 8A is a front view of the sampling device 1 as seen from the left in FIG. 4B;

FIG. 8B is a cross-sectional view taken along the line C-C of FIG. 8A;

FIGS. 9A to 9E are different views of a gasket member of the valve member of the sampling device of FIG. 1;

DETAILED DESCRIPTION OF THE DRAWINGS

Figure 1:
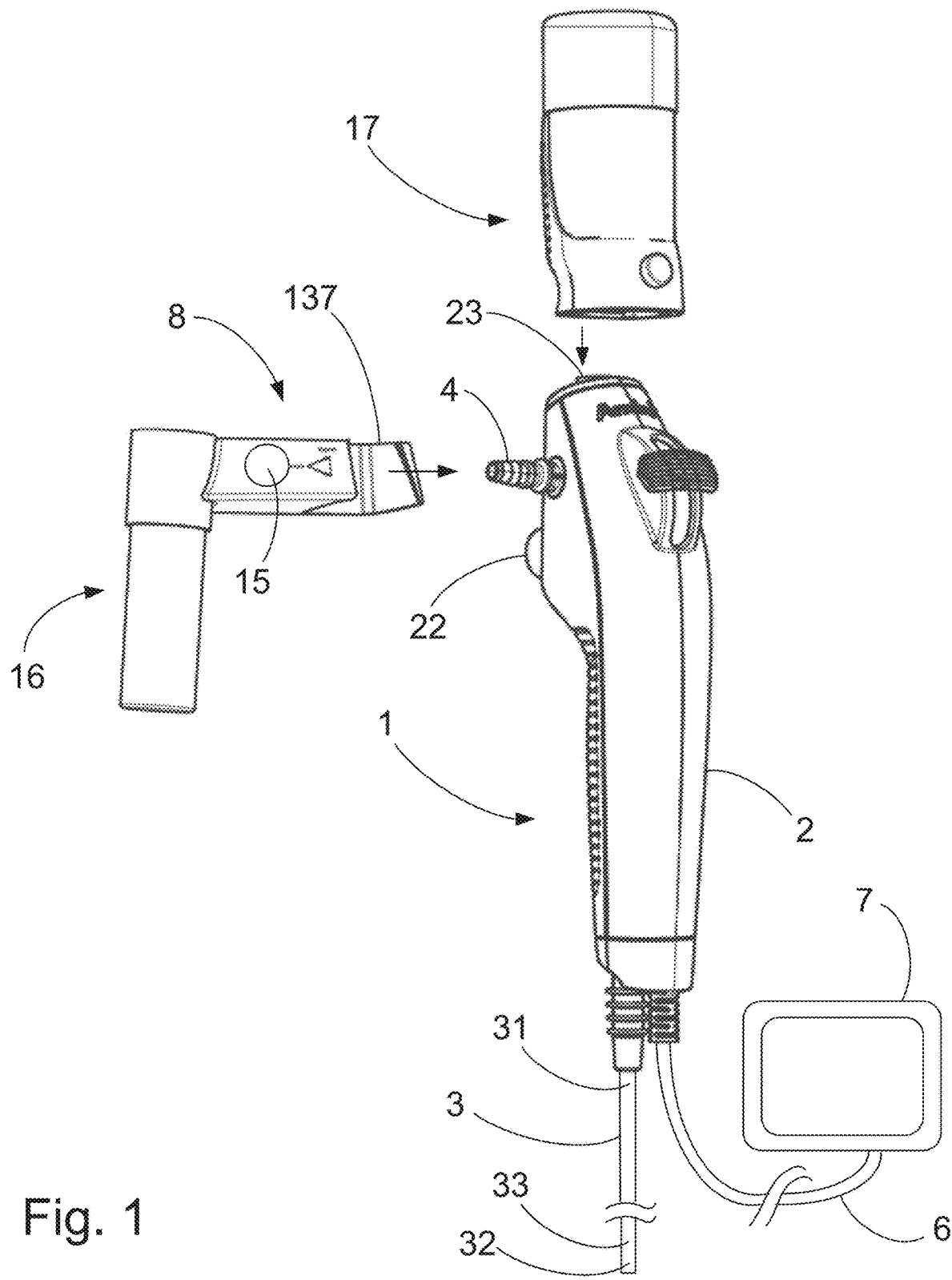
FIG. 1 is a perspective view of an endoscope connected to a schematically drawn monitor as well as a schematically drawn medical sampling device according to the first aspect of the invention connected to a sample container, and a saline cartridge shown not connected to the endoscope.

Referring to FIG. 1, an endoscope 1, a medical sampling device 8, and a saline cartridge 17 are shown. The endoscope 1, the medical sampling device, and the sample container 16 are adapted to and intended for single use. The medical sampling device 8 may be connected to a catheter instead of the endoscope 1.

The endoscope 1 is a medical device suitable for examination of natural and/or artificial body openings, e.g. for exploration of a lung cavity. The endoscope 1 comprises an operating handle 2, an insertion tube 3, and a suction connector 4. For illustration purposes, the insertion tube 3 is only shown in part in FIG. 1. The saline cartridge 17 is shown ready for connection to a suction channel 34 (shown in FIGS. 2 and 3) of the endoscope 1 via an inlet port 23 thereof.

The medical sampling device 8 includes a rotary knob 15 and a flange member 137. As shown, the sample container 16 is connected to the medical sampling device 8. The medical sampling device 8 is shown in detail in FIGS. 4A to 11E.

Figure 2:
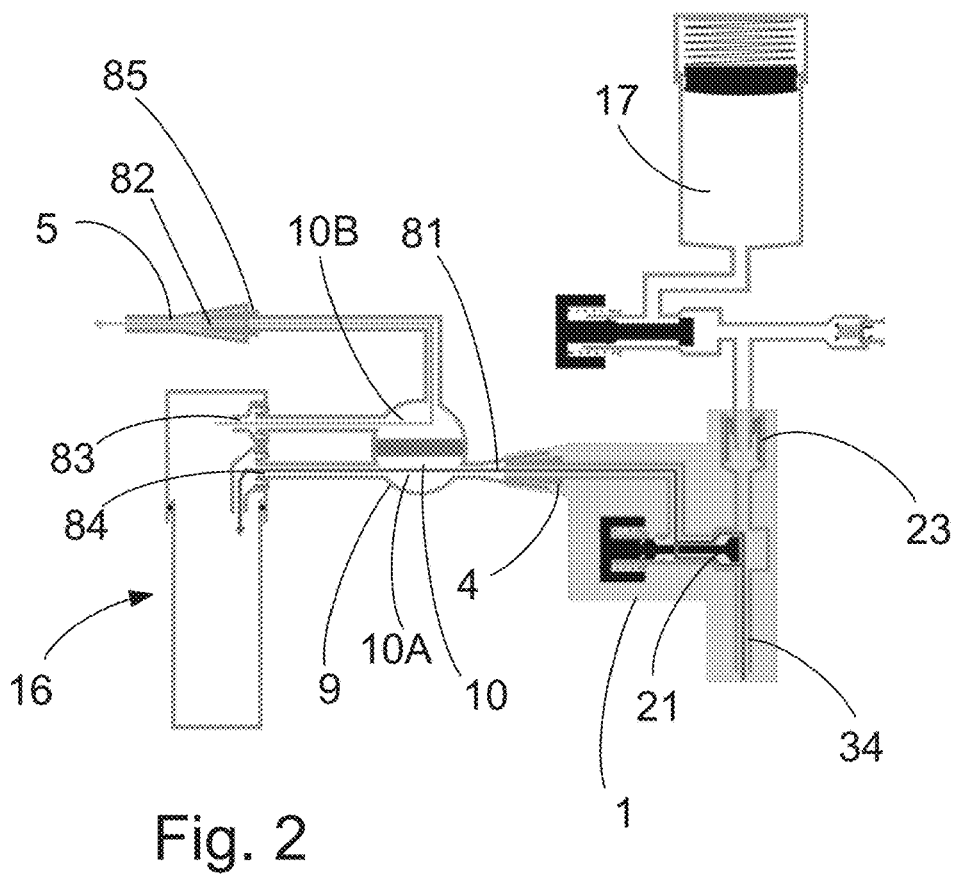
FIG. 2 is a schematic diagram of a sampling system comprising the parts of FIG. 1 in an assembled state and set to a first position of a valve member of the sampling device.
Figure 3:
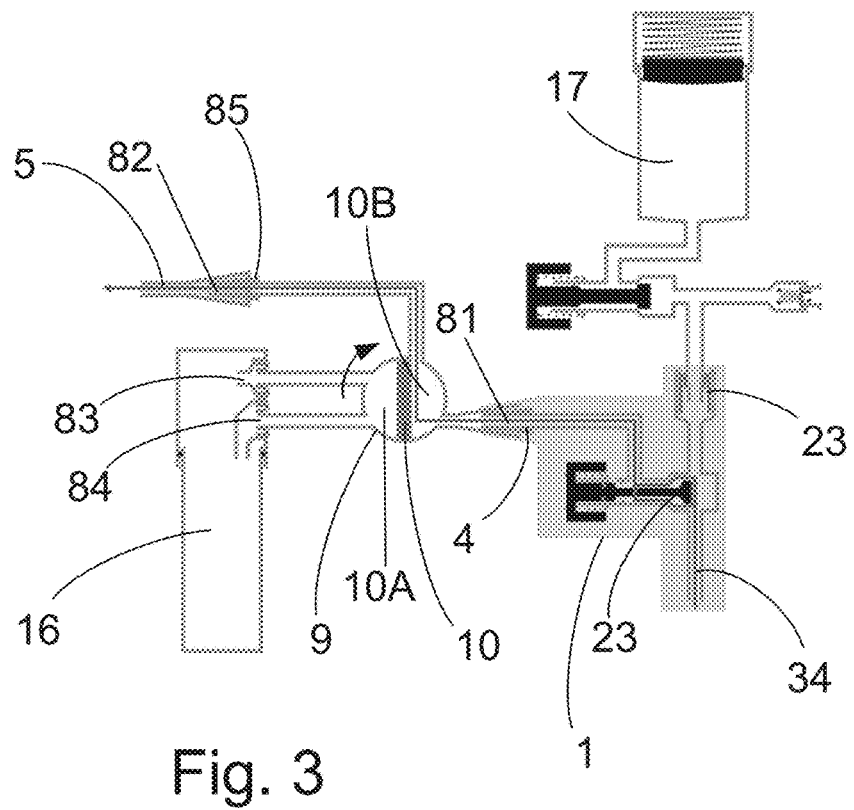
FIG. 3 is a schematic diagram of the sampling system of FIG. 2 set to a second position of a valve member of the sampling device.

FIGS. 2 and 3 are schematic diagrams of a sampling system comprising the parts of FIG. 1 in an assembled state and set to a first (FIG. 2) and a second (FIG. 3) position of a valve member 10 of the sampling device 8. In the first position fluid flows through the sample container 16 while in the second position the fluid bypasses the sample container 16.

Referring again to FIG. 1, the insertion tube 3 is an elongated member suitable for insertion into a patient, such as into a patient's lung through the patient's mouth. The insertion tube 3 extends from the operating handle 2 towards a distal end of the endoscope 1. The insertion tube 3 has a proximal end 31 connected to a handle housing of the handle 2 and a distal end 32 with a steerable, bendable tip part 33 allowing the insertion tube 3 to be maneuvered through the body cavities. Such body cavities may include trachea and bronchi of the patient, specifically in case of use of the medical system of FIG. 1 for bronchial or bronchoalveolar lavage, but, as will be appreciated by a person skilled in the art, the use of the medical sampling device according to the present invention is not necessarily limited to such procedures.

The distal tip of the tip part 33 comprises openings connected to one or more channels at least one of which, such as a suction channel, may be used as a suction channel 34 (shown in FIGS. 2 and 3). The suction channel 34 may be connected to a suction or vacuum source via the suction connector 4 by the activation of a valve 21 (shown in FIGS. 2 and 3) operated by a push-button 22 on the handle 2 of the endoscope 1 in a well-known manner. The tip part 33 furthermore includes a light source and a camera connected via a cable 6 to the monitor 7, allowing the operator and others to monitor the actions performed within the patient.

The suction connector 4 is of a standard type for attaching a flexible suction tube, which is in turn to be connected to a vacuum or suction source, e.g. a wall suction as is often present in hospital rooms. The suction connector 4 is a generally tubular, frustoconically shaped male connector provided with a taper to allow easy connection of the flexible suction tube and with circumferential corrugations or barbs allowing a secure connection of the flexible suction tube in a well-known manner. The connector 4 need not be an integral part of the endoscope 1; in some alternative endoscopes, the connector is a separate, interchangeable part. Furthermore, in some alternative endoscopes, the connector may be a receptacle or a socket, i.e. a female connector.

FIG. 1 also shows the medical sampling device 8, which is an embodiment of the first aspect of the invention, and the saline cartridge 17, both adapted to be attached to the endoscope 1 by a movement in respective directions of the arrows in the figure, whereby the saline cartridge 17 is positioned into fluid communication with the working channel or suction channel 34 thereof.

In the sampling system illustrated schematically in FIGS. 2 and 3, rather than connecting a flexible suction tube directly to the suction connector 4, the sampling device 8 is connected to the suction connector 4. The sampling device 8, in turn, is then connected to a flexible suction tube 5. For this purpose, the sampling device 8 has an identical, similar or at least corresponding tube connector or suction connector 85, to which the flexible suction tube 5 may be attached, and an opening or receptacle constituting a suction inlet 81 acting as a socket for receiving and securing the suction connector 4. Evidently, if the connector 4 is a separate, interchangeable part as mentioned above, the sampling device 8 could be adapted to fit directly into the endoscope 1 so as to entirely avoid the suction connector.

The sampling device 8 further comprises a sample container connector 139 comprising a sampling inlet 84 and a sampling outlet 83 adapted to engage and be inserted through the wall of the preferably detachable sample container 16, preferably through openings covered by a membrane. Preferably, the sample container 16 is adapted to self-seal when the sample container 16 is detached from the sampling device 8.

The saline cartridge 17 is adapted to be attached to the endoscope 1 in fluid communication with the suction channel 34 thereof via the inlet port 23 of the endoscope 1. The saline cartridge 17 is a canister pre-filled with a saline solution and with a known pressurization device for exerting pressure on the saline solution.

Figure 4A:
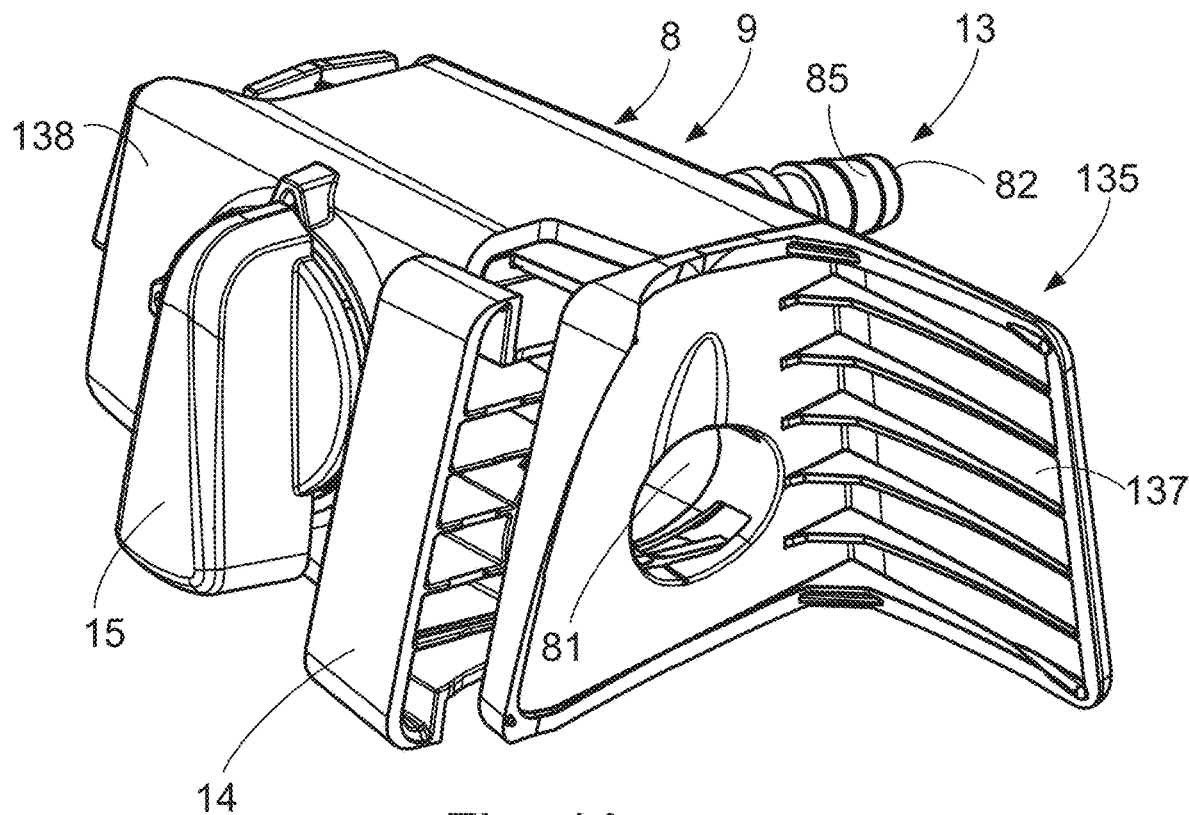
FIGS. 4A and 4B are perspective views of the sampling device of FIG. 1 set to a second position of a valve member of the sampling device and illustrating movement of a locking member from an unlocked position in FIG. 4A to a locked position in FIG. 4B.
Figure 4B:
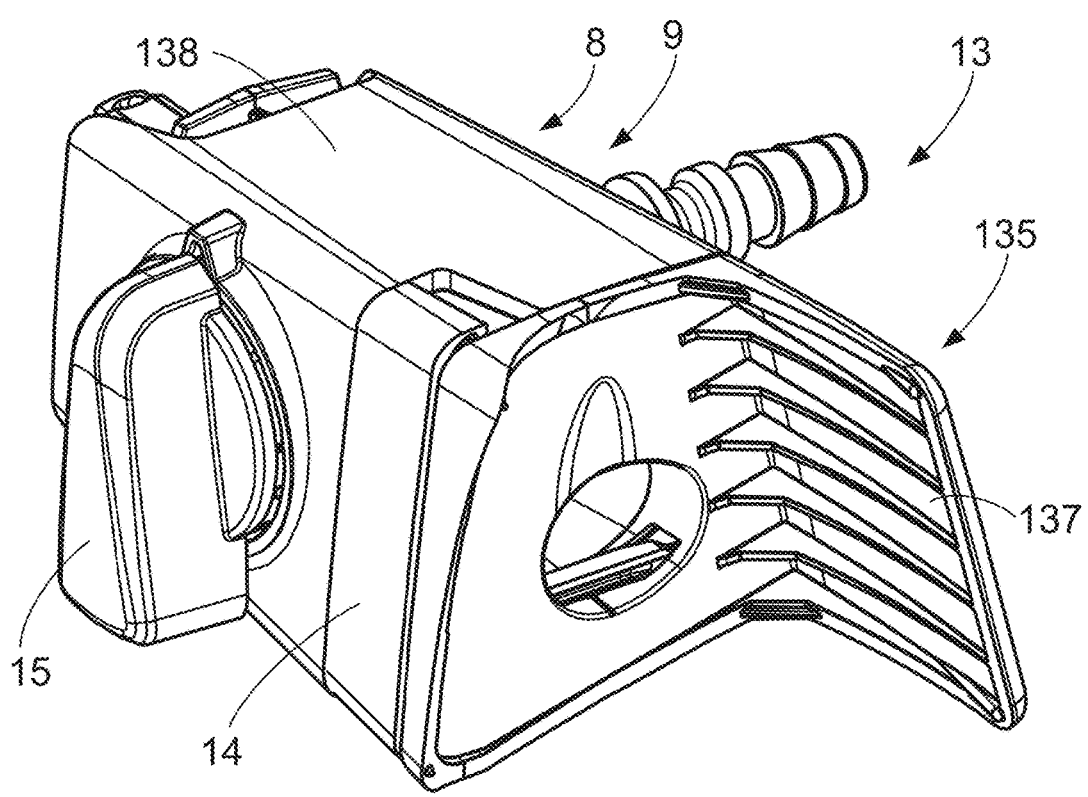

Now referring to all of the figures, the sampling device 1 comprises a suction inlet 81 for connection to the suction connector 4, a suction outlet 82 for connection to a vacuum source, the sampling outlet 83 for connection to the sample container 16, the sampling inlet 84 for connection to the sample container 16, and a valve 9 having a valve member 10 and a valve housing 13 (best seen in FIGS. 4A and 4B).

The valve member, specifically a gasket member 11 thereof (best seen in FIG. 7), has a first 10A and a second 10B chamber, see especially FIGS. 9B and 9E, and is rotatable in relation to the valve housing 13 between a first and a second position, the first position being illustrated in FIG. 2, the second in FIG. 3. In the first position, the first chamber 10A establishes fluid communication between the suction inlet 81 and the sampling inlet 84, and the second chamber 10B establishes fluid communication between the sampling outlet 83 and the suction outlet 82. In the second position, the second chamber 10B establishes fluid communication between the suction inlet 81 and the suction outlet 82 by a 90° clockwise rotation of the rotary knob 15 in the view of FIG. 8A. Note that the sampling device 8 could work in a similar manner by rotating 90° counter-clockwise, in which case the first chamber 10A would establish fluid communication between the suction inlet 81 and the suction outlet 82.

In the first and second positions, respectively, the valve member 10 substantially blocks all other fluid communication between the inlets and outlets 81-84 of the sampling device 8.

Figure 7:
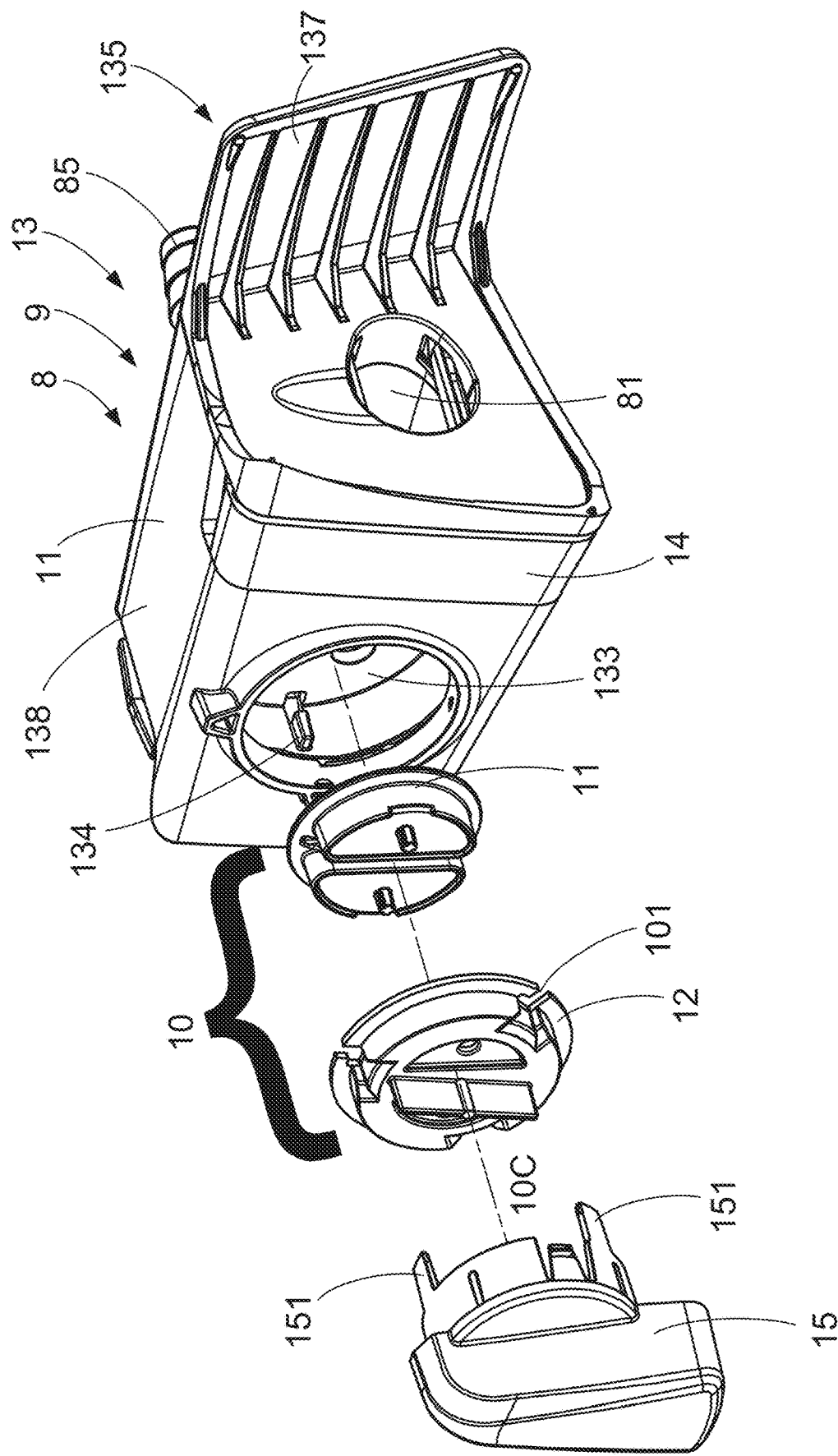
FIG. 7 is an exploded perspective view similar to those of FIGS. 4A and 4B of the sampling device of FIG. 1 in an unassembled state illustrating assembly of the sampling device.

The valve housing 13 is a stationary part of the medical sampling device 8 in relation to which the valve member 10 is rotatable about a rotation axis 10C, see FIG. 7. This stationary part is fixated to and held stationary in relation to the endoscope handle 2 when the medical sampling device 8 is fixated to the endoscope 1.

The valve housing 13 comprises a valve housing part 135, which includes the suction inlet 81, a channel for connecting the suction inlet 81 to the suction connector 85 and the suction outlet 82, a channel for connecting the suction outlet 82 to the sampling outlet 83, a sliding spacing 136 for a slideable locking member 14, a flange member 137, and a valve member spacing 133 in which the valve member 10 is positioned. All of these are integrally provided in the valve housing part 135. The valve housing 13 also comprises a valve housing shell 138 which is positioned to surround the valve housing part 135 to form some of the outer surfaces of the valve housing 13.

During assembly of the medical sampling device 1, the valve member 10 is first positioned in the valve member spacing 133, after which the valve housing shell 138 is positioned to partially cover the valve member 10, to hold the valve member 10 in position, and to cover the valve housing part 135. The rotary knob 15 is then positioned afterwards to be attached to and rotatable in relation to the valve housing 13 together with the valve member 10. The valve housing shell 138 is snapped onto the valve housing part 135 in an irreversible manner. Each of the valve housing part 135 and the valve housing shell 138 is one, integrally moulded part.

The valve housing part 135 comprises a circumferentially extending seal surface 131 at a bottom of the valve member spacing 133, see FIG. 5A, the valve member 10 comprising a corresponding seal surface 102, see especially FIGS. 9A, 9B, and 9E, the seal surfaces 131, 102 abutting each other and sealing the chambers 10A, 10B and interior parts of the valve 9, in which fluid flows, such as the channels and valve ports as described below, from the surroundings. The seal surface 102 is provided on an interior part in the form of a gasket member 11 of the valve member 10 and extends along peripheral walls 115 of the valve member 10 and along a linear wall 114 separating the two chambers 10A, 10B, see also further below.

The valve housing part 135 comprises the suction inlet 81, the suction outlet 82, the sampling outlet 83, and the sampling inlet 84, which are each provided as a fluid port in a surface of the valve housing 13, specifically of the valve housing part 135, and, thus, of the sampling device 1. The suction inlet 81 is positioned at a distance in a radial direction from the rotation axis 10C and from the valve member 10, so that an insertion direction of the suction connector 4 of the endoscope 1 is aligned with said direction. Similarly, the sampling inlet 84 and outlet 83 are positioned a distance in a radial direction from the rotation axis 10C and from the valve member 10, so that an insertion direction of a sample container connector 139 of the valve housing part 135 is aligned with said direction. The sample container connector 139 comprises the sampling inlet 84 and sampling outlet 83, see especially FIG. 6B. The suction outlet 82 is positioned a distance from the valve member 10 in an axial direction of the rotation axis 10C, so that an insertion direction of the suction connector 85 into a suction tube of a vacuum source is aligned with said direction.

Referring to FIG. 7, when assembling the sampling device 1, the valve member 10 is moved into position into the valve member spacing 133 by a shifting movement in an axial direction of the rotation axis 10C so that three projections 134 projecting from a valve housing surface 132 fit into respective three recesses 101 in a periphery of the circular valve member 10, see also FIGS. 5A and 7 and further below. One or more valve member stopping elements may be provided on the valve member 10 and on the valve housing surface 132 to limit the rotational movement of the valve member 10, configured so that, when having rotated from the first to the second position, the valve member 10 is not allowed to rotate further in that direction, and when having rotated from the second to the first position, the valve member 10 is not allowed to rotate further in that direction.

Each of the valve member 10, the gasket member 11, and the exterior part 12 are substantially disc-shaped and have a substantially circular shape. The gasket member 11 comprises the fluid-tight linear wall 114 separating the two chambers 10A and 10B from each other. The first and second chambers 10A, 10B are substantially cylindrical, with cylinder side surfaces extending in said axial direction defined by the rotation axis 10C, and are crescent-shaped in a cross-section normal to the rotation axis 10C, see especially FIG. 9C. The wall 114 consists of a linear wall of the exterior part 12 and two walls forming a recess of the gasket member 11, in which recess the linear wall of the exterior part is positioned, see FIGS. 7 and 9A to 10E. The wall 114 separates the two chambers 10A, 10B from each other so as to block fluid communication between the two chambers 10A, 10B. This wall 114 extends linearly in a cross-section perpendicular to the rotation axis 10C, providing linear sides of the crescent shapes of the respective chambers 10A, 10B. Respective semi-circular walls 115 form the rounded parts of the crescent shapes. These walls 115 form part of a circumferential wall of the valve member 10 extending along a cylinder side surface in the axial direction of axis 10C.

Referring especially to FIGS. 9A to 9E, the gasket member 11 further comprises a circumferentially and peripherally extending, circular lip 113 extending between and being compressed between a circumferentially and laterally or radially, outwardly protruding, peripheral edge 121 of the exterior part 12 and the seal surface 131 of the valve housing 13. The lip 113 extends outwardly from the semi-circular walls 115 in an entire circumference of the gasket member 11. The lip 113 is shown in an uncompressed state in FIGS. 9A to 9E.

Figures 10A, 10B:
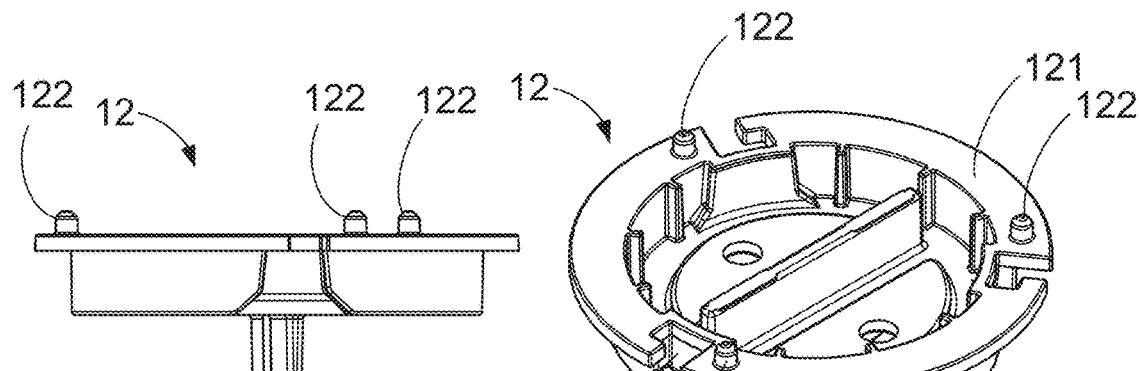
FIGS. 10A to 10E are different views of an exterior part of the valve member of the sampling device of FIG. 1.
Figures 10C, 10D:
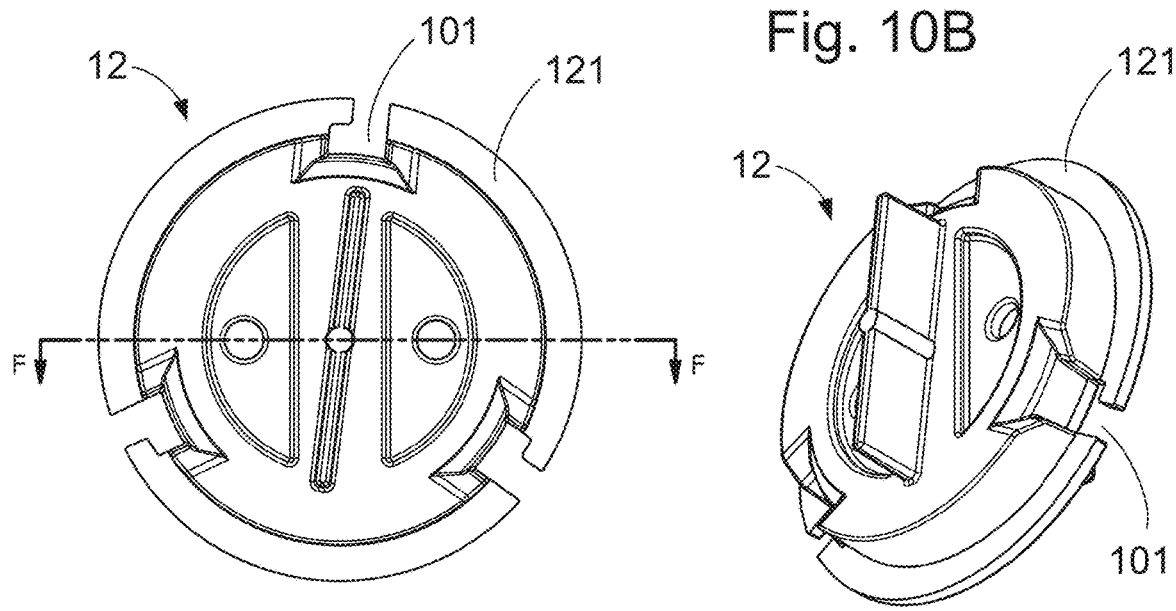
Figure 10E:
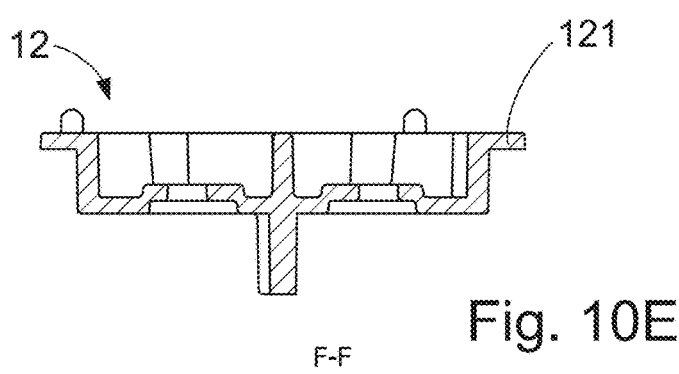
Figure 11A:
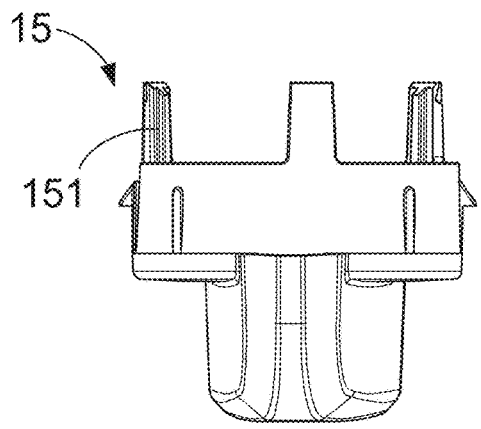
FIGS. 11A to 11E are different views of a rotary knob of the valve member of the sampling device of FIG. 1.
Figure 11B:
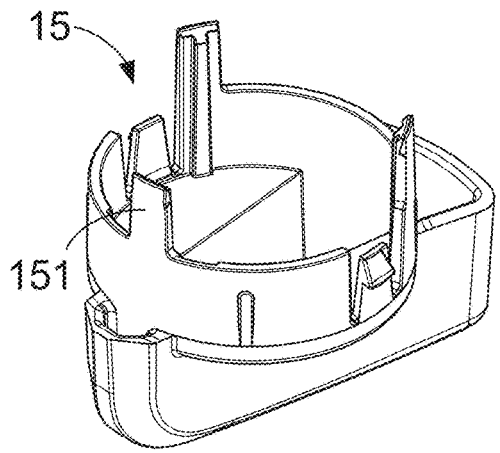
Figure 11C:
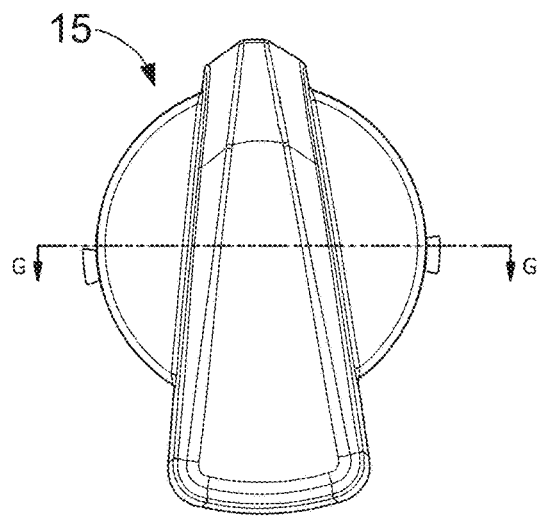
Figure 11D:
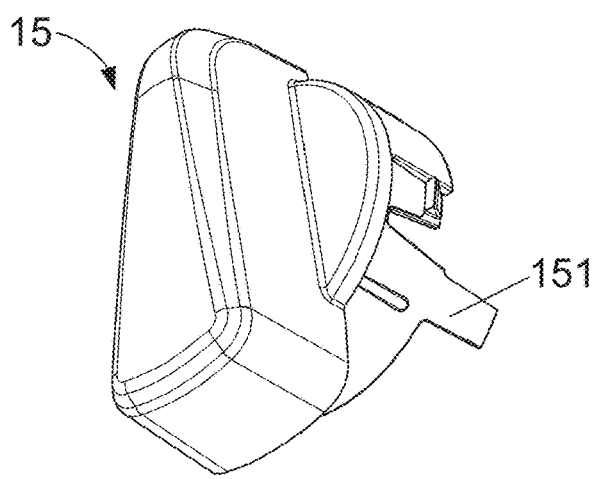
Figure 11E:
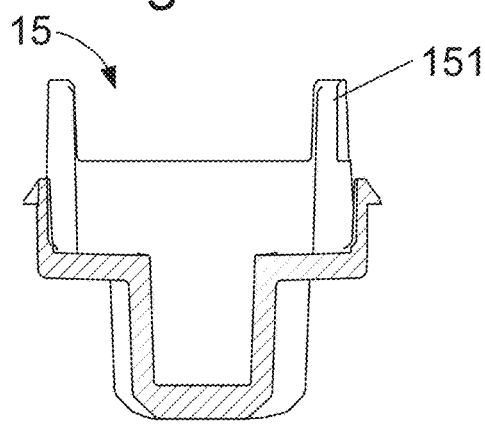

Referring especially to FIGS. 10A and 10B, the exterior part 12 further comprises three protrusions 122 protruding from the peripheral edge 121 of the exterior part 12, so that, in the assembled state, the protrusions extend towards the valve housing surface 132. The protrusions are located at a greater radial distance on the peripheral edge 121 than the outer diameter of the gasket member 11, so that if the rotary knob 15 or exterior part 12 is pushed towards the valve housing surface 132, the protrusions 122 abut the valve housing surface 132 preventing pinching of the gasket member 11, which could otherwise cause a leakage.

Figure 5A:
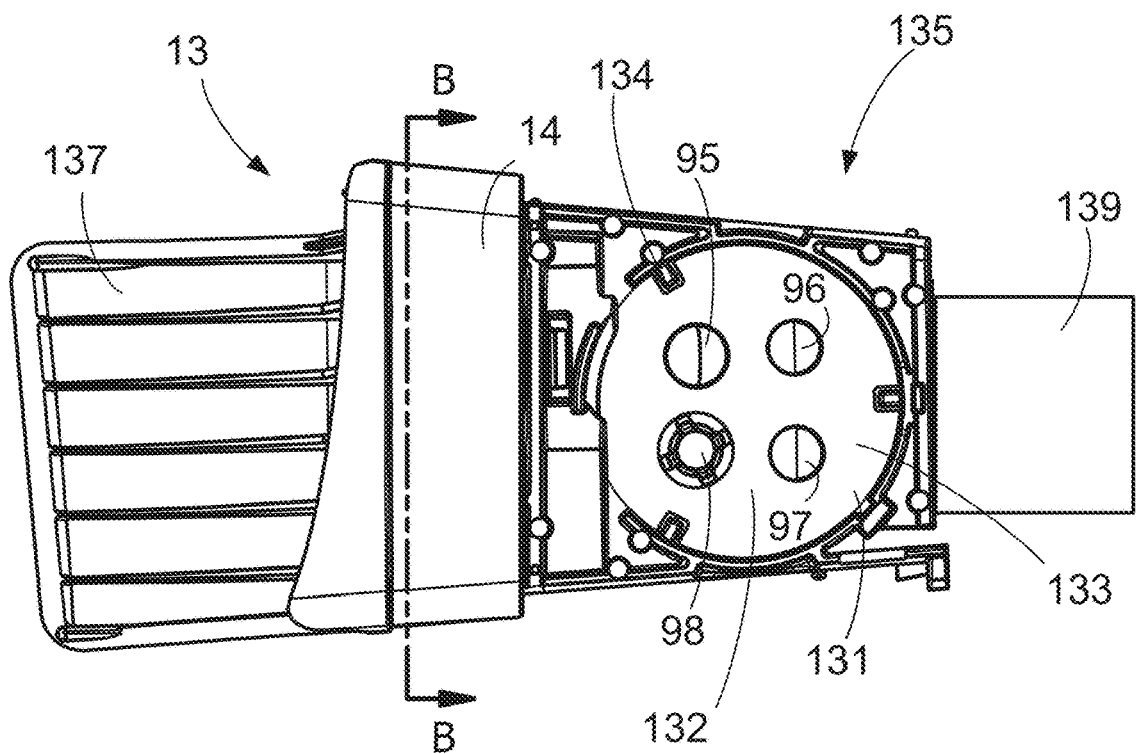
FIG. 5A is a front view of a valve housing part and the locking member of the sampling device of FIG. 1 as seen from the left side in FIGS. 4A and 4B.
Figure 5B:
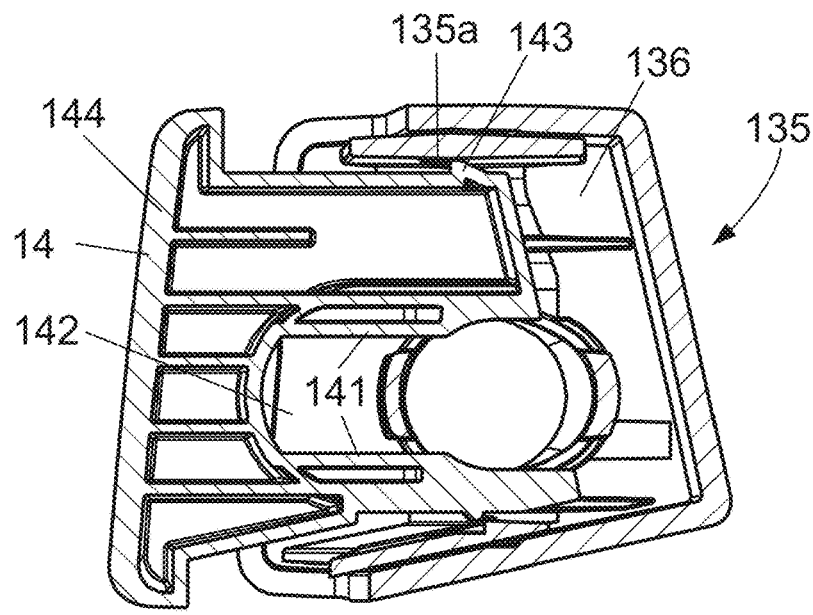
FIG. 5B is a cross-sectional view taken along the line B-B of FIG. 5A.
Figure 6A:
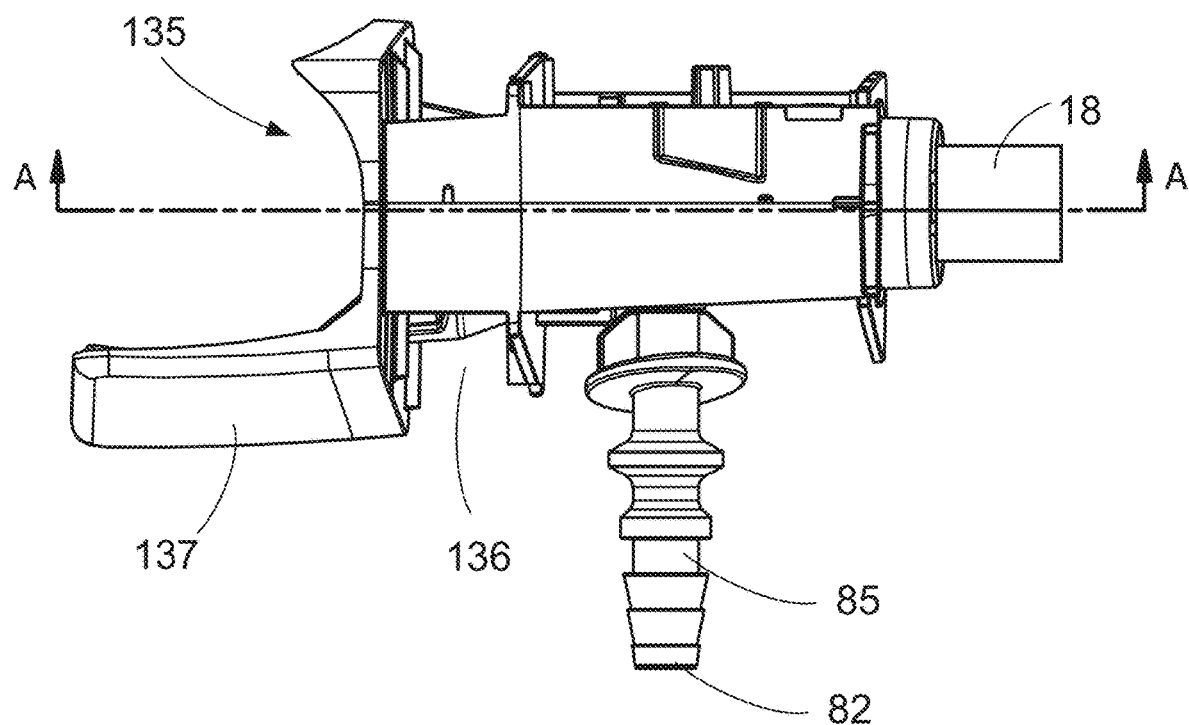
FIG. 6A is a bottom view of the valve housing part of FIG. 5A as seen from a bottom of FIG. 5A.
Figure 6B:
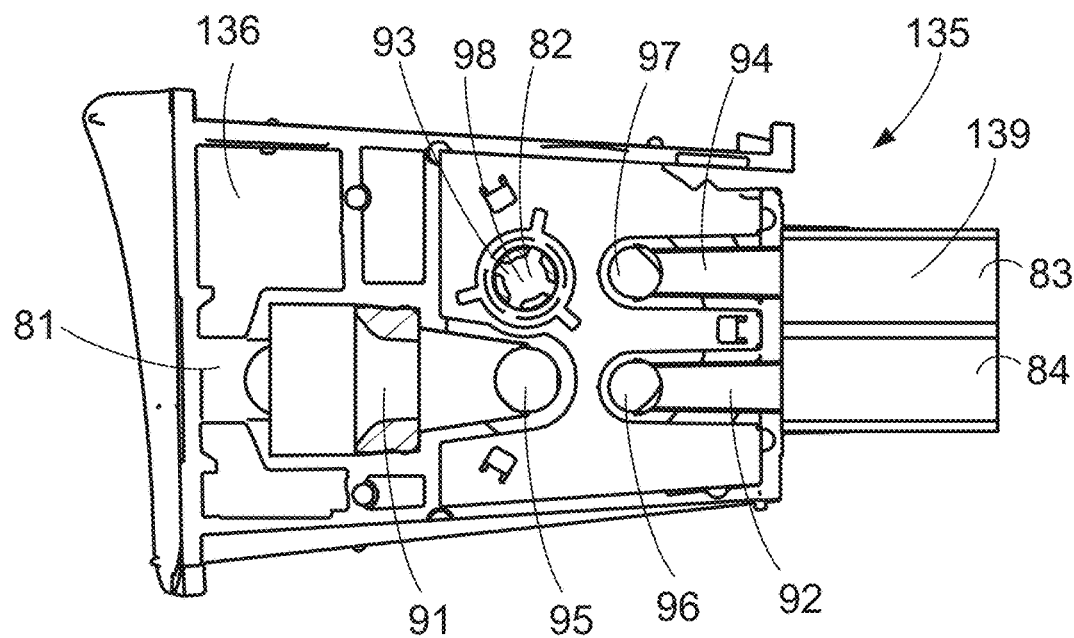
FIG. 6B is a cross-sectional view taken along the line A-A of FIG. 6A.

Referring especially to FIGS. 5A and 6B, the valve housing part 135 comprises a number of internal fluid channels or conduits 91-94 allowing for fluid flow through the sampling device 1 and connecting the inlets and outlets 81-84 to valve ports 95-98 of the valve 9, the valve ports 95-98 establishing fluid communication between the respective channels 91-94 and the first 10A and second 10B chambers, depending on the rotary position of the valve member 10 as described above. These channels 91-94 are provided to be fluid tight in relation to each other. Thus, a first suction channel 91 connects the suction inlet 81 to a first valve port 95, a first sampling channel 92 connects the sampling inlet 84 to a second valve port 96, a second sampling channel 94 connects the sampling outlet 83 to a third valve port 97, and a second suction channel 93 connects the suction outlet 82 to a fourth valve port 98. The first to fourth valve ports 95-98 are configured so as to be distributed in sequence in a clockwise circumferential direction about the rotation axis 10C when seen as in FIG. 5A.

Each of the first and second chambers 10A, 10B comprises a top opening 111A, 111B, respectively, see especially FIGS. 9B and 9E. Each of these top openings 111A, 111B may alternatively be provided as two or more top openings of one or each chamber 10A, 10B. Each of the first and second chambers 10A, 10B comprises a bottom surface 112A, 112B, respectively, positioned oppositely from the respective top opening 111A, 111B, and respective lateral interior surfaces of walls 115 surrounding and connected to the respective bottom surface 112A, 112B, these bottom and lateral surfaces establishing fluid-tight internal surfaces of the respective chambers 10A, 10B.

In said first position of the valve member 10, the top opening 111A is aligned with the first 95 and second 96 valve ports, providing fluid communication between the suction inlet 81 and the sampling inlet 84, and the top opening 111B is aligned with the third 97 and fourth 98 valve ports, providing fluid communication between the sampling outlet 83 and the suction outlet 82. In said second position (as shown in FIGS. 4A and 4B) of the valve member 10, the top opening 111B is aligned with the first 95 and fourth 98 valve ports, and the top opening 111A is aligned with the second 96 and third 97 valve ports.

Referring to FIG. 5A, the valve ports 95-98 are provided in the valve housing surface 132 of the valve housing part 135. This surface 132 is plane and extends in a plane extending in radial directions in relation to the rotation axis 10C. Hereby, the valve ports 95-98 are configured to be suitably aligned with the top openings 111A, 111B. The seal surface 131 of the valve housing part 135 is also included in this plane surface to surround all four valve ports 95-98.

Referring to FIG. 6B, the channels 91, 92, 94 each comprises a bent section of approximately 90 degrees, allowing each channel to extend from the respective valve port and to the respective inlet or outlet.

The valve housing 13 and the exterior part 12 are manufactured from POM. The gasket member 11 is manufactured from KRAIBURG® TPE, MC/LF Series, tradename TERMOLAST® M, type TM7LFT as mentioned above.

The gasket member 11 is provided as one, integral member, which surrounds the first chamber 10A and surrounds the second chamber 10B, and which separates the first and second chambers from each other via the linear wall 114 separating the first 10A and second 10B chambers.

Hereby, the sampling device 8 is configured so that when a vacuum pressure from the vacuum source is exerted on the second chamber 10B in the first and second positions of the valve member 10, the vacuum pressure pulls at least the gasket member 11 towards the fourth valve port 98 and the suction outlet 82. To achieve this, the gasket member 11 is provided separately from and movably attached to the exterior part 12 so as to be slideable in relation to, in the axial direction of, the valve member 10, see especially FIGS. 9A to 10E. The gasket member 11 defines the first and second chambers 10A, 10B on all sides except at the respective top openings 11A, 11B, so that when a vacuum pressure is exerted on the suction outlet 82 in the first and the second positions, the vacuum pressure causes the gasket member 11 or parts thereof to move and/or be sucked in the direction towards the suction outlet 82.

The rotary knob 15, rotatable by hand, is attached to be rotationally fixed to the exterior part 12 of the valve member 10. The gasket member 11 is rotationally fixed to the exterior part 12 so that both members 11, 12 rotate when the exterior part 12 is rotated by means of the knob 15.

The suction inlet 81 is a female connector forming a socket defining an insertion direction adapted to receive the suction connector 4 in an insertion direction for forming a fixed connection. The sampling device 8 is, furthermore, adapted to engage the endoscope 1 in a manner preventing rotation around the suction connector 4.

The sampling inlet 84 is provided in a sample container connector 18 adapted for connection to the sample container 16. The sample container connector 18 extends in a direction parallel to said insertion direction.

The sampling device 8 is adapted to be fixated to the endoscope 1 by means of the locking member 14, which is slideable in and in relation to the valve housing part 13 between the locked position shown in FIG. 4B, in which the sampling device 8 is fixated to the endoscope 1, and the unlocked position shown in FIG. 4A, in which the sampling device 8 can be positioned to be fixated to or be released from the endoscope 1.

As is seen best in FIG. 8B, the suction connector 4 is of the type comprising one or more circumferentially extending barbs for engaging and maintaining connection to a tube. The locking member 14 is configured to engage one such barb of the suction connector 4. For this purpose, the locking member 14 comprises two locking supports 141 that are slideable into engagement with the barb of the suction connector 4 when the suction connector 4 is inserted into the suction inlet 81 socket, see FIG. 5B. The locking member 14 comprises a cut-out 142 allowing for sliding of the locking member 14 into the locked position, the suction connector 4 extending through the cut-out 142 in said locked position of the locking member 14. The locking supports 141 can be considered projections extending into or towards the cut-out 142 so that the locking supports 141 are slid into the locked position of the locking member 14 by being slid to a position abutting the barb of the suction connector 4 after insertion of the suction connector 4.

The locking member 14 is provided as a part separate from the valve housing 13 and is attached to be slideable in relation to the valve housing 13, but not detachable from the valve housing 13. A barb 143 of the locking member 14 engages a corresponding barb 135a of the valve housing part 135 when in the unlocked position, so that the locking member 14 is prevented from being removed from the valve housing 13 when in the unlocked position, see FIG. 5B.

The locking member 14 further comprises an engagement part 144, which in the released position extends out of the valve housing 13, making it possible to slide the locking member 14 between the locked and released positions by a hand pushing or pulling the locking member 14. The engagement part 144 is provided substantially inside the valve housing 13 when the locking member 14 is in the locked position, an outer surface of the engagement part 144 being substantially flush with an outer surface of the valve housing 13. The engagement part 144 comprises a grabbing projection allowing for grabbing the locking member 14 by means of a finger to pull the locking member 14 towards the released position.

The valve housing part 135 further comprises the flange member 137, which is configured to match a shape or outer surfaces of the endoscope handle 2. In the fixated position of the sampling device 8, the flange member 137 is configured to extend around part of the handle 2, inner surfaces of the flange member 137 abutting outer surfaces of the handle 2 to ensure the fixation of the sampling device 8 against movement with respect to the handle 2 when the sampling device 8 is locked to the endoscope handle 2 by means of the locking member 14 as described in the above.

Referring especially to FIGS. 7 and 8B, the sampling device 8 may be assembled in accordance with a method according to the second aspect of the invention in the following manner: The valve member 10 is positioned in the valve member spacing 133 so as to be rotatable in relation to the valve housing 13 between the first and a second positions of the valve member 10. Before or after or simultaneously with the former step, the gasket member 11 is positioned so as to be slideably attached to the exterior part 12 as explained, and the rotary knob 15 is attached to the valve housing 13 and the exterior part 12.

Referring especially to FIGS. 7 and 11A to 11E, the rotary knob 15 comprises three legs 151 that engage the slots 101 positioned along a periphery of the exterior part 12 in order to fixate the exterior part 12 and the rotary knob 15 to each other and to allow the rotary knob 15 to rotate the valve member 10 on rotation of the rotary knob 15.

Referring to FIGS. 2 and 3, operation of the shown sampling system is carried out as follows:

The operator activates the saline cartridge 17 to expel liquid through the inlet port 23 of the endoscope 1. The expelled liquid is dispensed into the suction channel 34 and instilled at the desired location in the patient at the distal end 32. Having instilled the saline solution in the patient, a fluid sample can now be extracted using the part of the system comprising the endoscope 1, the sampling device 8, the sample container 16 and the flexible suction tube 5 connected to the suction source in the manner explained in the following.

If not already in the first position, an operator turns the valve member 10 via the rotary knob 15 to the first position as shown in FIG. 2. The operator then presses a push-button 22 of the endoscope 1 so as to open the valve 21 of the endoscope and, thus, a passage through the suction channel 34 of the endoscope 1. Liquid, or rather a fluid comprised of air, liquid, and potentially solid tissue samples, from the sampling site, e.g. in the lungs, will now be drawn through the suction channel 34 via the valve 21 to the suction connector 4, further to the suction inlet 81, further to the first chamber 10A, out of the sampling outlet 83 and into the sample container 16. In the sample container 16, a main part of the liquid and tissue samples will be trapped as they fall to the bottom under the influence of gravity, whereas the remainder of the fluid, mostly air, will be sucked out through the sampling outlet 83, to the second chamber 10B, to the suction outlet 83 and away via the suction tube 5.

When a sample of suitable volume has accumulated in the sample container 16, the push-button 5 is released, and the valve 22 closes.

The sample container 16 may now be removed and possibly replaced with a new and empty one, and the process may be repeated.

When no more samples need be taken, the valve member 10 is turned via rotary knob 15 to the second position shown in FIG. 3 to shunt the passage though the sample container 16. Fluid from the sampling site will now be drawn through the suction channel 34 via the valve 21 to the suction connector 4, further to the suction inlet 81, further to the second chamber 10B, to the suction outlet 83 and away via the suction tube 5. Normal suction of the fluid through the suction channel 34 may then be performed without having to remove the sampling device 8, i.e. normal operation with the endoscope 1, which may be unrelated to the sampling, may still be performed without having first to remove the sampling device 9. Furthermore, placing the valve member 10 in this bypass or shunt position also allows the user to prevent any sample loss by directing the flow directly to the wall suction without removing the sample container 16 from the assembly, e.g. if the user anticipates movement. By disengaging the shunt by resetting the valve member 10 to the first position, the operator will be able to continue sampling.

After the sampling procedure is completed, the endoscope 1 and the sampling device 8 may be disposed of.

The use of the sampling device 8 and the sample container 16 are independent on the use of the, therefore, optional saline cartridge 17. A suitably sized syringe may instead be attached to the inlet port 23 to provide the liquid.

In an embodiment of the third aspect of the invention, the sampling device 8 is used for sampling of bodily fluids and/or bodily tissue as described above.

In an embodiment of the fourth aspect of the invention the sampling device 8 is used for connection with or attachment to the endoscope 1 for flushing and/or for sampling of bodily fluids and/or bodily tissue and/or for connection with or attachment to the sample container 16 as described above.

An embodiment of the fifth aspect of the invention involves a medical kit comprising the sampling device 8 as well as the endoscope 1 and/or the sample container 16 as described above.

An embodiment of the sixth aspect of the invention involves a medical system comprising the endoscope 1, the sampling device 8 attached to the endoscope 1, and the sample container 16 attached to the sampling device 8 as described above.

An embodiment of the seventh aspect of the invention involves a method as described above of assembly of the latter medical system, comprising: connecting the suction connector 4 to the suction inlet 81 of the sampling device 8, fixating the sampling device 8 to the handle 2 of the endoscope 1, connecting the suction outlet 82 to a vacuum source, and connecting the sampling inlet 84 and sampling outlet 83 to the sample container 16.

Following are specific examples of the embodiments described above.

Example 1. A medical sampling device for use with an endoscope or catheter for flushing of a body cavity and/or for sampling of bodily fluids and/or bodily tissue, the endoscope or catheter having a suction channel and a suction connector in fluid communication with said suction channel, the sampling device comprising
a suction inlet for connection to the suction connector,
a suction outlet for connection to a vacuum source,
a sampling outlet for connection to a sample container,
a sampling inlet for connection to the sample container, and
a valve having a valve member and a valve housing,
wherein the valve member has a first and a second chamber and is rotatable in relation to the valve housing between a first and a second position,
the first chamber in the first position establishing fluid communication between the suction inlet and the sampling inlet,
the second chamber in the first position establishing fluid communication between the sampling outlet and the suction outlet, and
one of the first and the second chamber in the second position establishing fluid communication between the suction inlet and the suction outlet.

Example 2. The medical sampling device according to example 1, wherein the sampling device is configured so that when a vacuum pressure from the vacuum source is exerted on the second chamber in the first position and on the first or second chamber in the second position, the vacuum pressure pulls at least a part of the valve member towards the suction outlet.

Example 3. The medical sampling device according to example 1 or 2, wherein the valve member comprises an exterior part and an interior part, and the interior part is a gasket member provided separately from and movably attached to the exterior part so as to be movable in relation to, in an axial direction of, the valve member, the gasket member laterally surrounding the first and/or the second chamber so that when a vacuum pressure is exerted on the suction outlet in the first and/or the second position, the vacuum pressure causes the gasket member to move in the direction towards the suction outlet.

Example 4. The medical sampling device according to example 3, wherein each of the first and second chambers comprises at least one top opening providing said fluid communication between the respective inlets and outlets in the first and second positions of the valve member via the respective first and second chambers, a bottom surface positioned oppositely from the top opening, and lateral surfaces surrounding and connected to the bottom surface, the bottom and lateral surfaces establishing internal surfaces of the respective chamber, and wherein the lateral surfaces and/or the bottom surface are provided as parts of the gasket member.

Example 5. The medical sampling device according to example 3 or 4, wherein the gasket member comprises a lip extending at least partly between and/or being compressed between the exterior part and a seal surface of the valve housing.

Example 6. The medical sampling device according to any one of the previous examples, wherein the valve member is rotatable about an axis defining an axial direction, and a first valve port connected to the suction inlet and/or a second valve port connected to the sampling outlet and/or a third valve port connected to the suction outlet and/or a fourth valve port connected to the sampling inlet is/are provided in a valve housing surface extending substantially radially in relation to the axial direction.

Example 7. The medical sampling device according to any one of the previous examples, wherein the medical sampling device is configured to be fixated to the endoscope when connected to the suction connector thereof.

Example 8. The medical sampling device according to example 7, wherein the medical sampling device is adapted to be fixated to the endoscope when connected to the suction connector thereof by means of a moveable locking member.

Example 9. A method of assembly of a sampling device according to any one of the previous examples, comprising the steps of:
providing a valve member having a first and a second chamber,
providing a valve housing having a suction inlet, suction outlet, sampling outlet, and sampling inlet; and
attaching the valve member in a valve member spacing of the valve housing so as to be rotatable in relation to the valve housing between a first and a second position, so that the first chamber in the first position establishes fluid communication between the suction inlet and the sampling inlet, the second chamber in the first position establishes fluid communication between the sampling outlet and the suction outlet, and the first chamber or second chamber in the second position establishes fluid communication between the suction inlet and the suction outlet.

Example 10. A method according to example 9, comprising the further step of attaching a rotary knob to the valve housing and/or valve member so that the valve member may be rotated between the first and second positions by means of rotation of the rotary knob.

Example 11. Use of a medical sampling device according to any one of examples 1 to 8 for sampling of bodily fluids and/or bodily tissue.

Example 12. Use of a medical sampling device according to any one of examples 1 to 8 for connection with or attachment to an endoscope for flushing and/or for sampling of bodily fluids and/or bodily tissue and/or for connection with or attachment to a sample container.

Example 13. A medical kit comprising a medical sampling device according to any one of examples 1 to 8 as well as an endoscope or a catheter adapted for attachment to said sampling device and/or a sample container adapted for attachment to said sampling device.

Example 14. A medical system comprising: an endoscope or a catheter having a suction channel and a suction connector in communication with said suction channel, a medical sampling device according to any one of examples 1 to 8 attached to the endoscope or catheter, and a sample container attached to the medical sampling device.

Example 15. A method of assembly of a medical system according to example 14, comprising the steps of:
  providing an endoscope having a handle, a suction channel and a suction connector in communication with said suction channel,
  providing a medical sampling device according to any one of examples 1 to 8,
  providing a sample container,
  providing a vacuum source,
  connecting the suction connector to the suction inlet of the sampling device,
  attaching or fixating the medical sampling device to the handle,
  connecting the suction outlet of the sampling device to the vacuum source, and
  connecting the sampling inlet and sampling outlet of the sampling device to the sample container.

LIST OF PARTS AND PART NUMBERS 1 endoscope
2 operating handle
21 endoscope valve
22 push button
23 inlet port
3 insertion tube
31 proximal end
32 distal end
33 steerable tip part
34 suction channel
4 suction connector
5 suction tube
6 cable
7 monitor
8 sampling device
81 suction inlet
82 suction outlet
83 sampling outlet
84 sampling inlet
85 suction connector
9 valve
91 first suction channel
92 first sampling channel
93 second suction channel
94 second sampling channel
95 first valve port
96 second valve port
97 third valve port
98 fourth valve port
10 valve member
10A first chamber
10B second chamber
10C rotation axis
101 recesses
102 seal surface
11 gasket member
111A top opening of chamber 10A
111B top opening of chamber 10B
112A bottom surface
112B bottom surface
113 lip
114 linear wall
115 semi-circular walls
12 exterior part
121 edge
122 protrusion
13 valve housing
131 seal surface
132 valve housing surface
133 valve member spacing
134 projections
135 valve housing part
135a edge
136 sliding spacing
137 flange member
138 valve housing shell
139 sample container connector
14 locking member
141 locking support
142 cut-out
143 barb
144 engagement part
15 rotary knob
151 legs
16 sample container
17 saline cartridge

What is claimed is:

1. A medical sampling device for use with a medical device having a suction channel and a suction connector in fluid communication with said suction channel, the medical sampling device comprising:
  a suction inlet adapted to be connected to the suction connector;
  a suction outlet adapted to be connected to a vacuum source;
  a sampling inlet adapted to be connected to a sample container;
  a sampling outlet adapted to be connected to the sample container; and
  a valve having a valve member and a valve housing, wherein the valve member has a first and a second chamber and is rotatable in relation to the valve housing between a first and a second position, wherein in the first position, the first chamber establishes fluid communication between the suction inlet and the sampling inlet and the second chamber establishes fluid communication between the sampling outlet and the suction outlet, and wherein in the second position, one of the first and the second chamber establishes fluid communication between the suction inlet and the suction outlet, wherein the valve member comprises an exterior part and an interior part, and the interior part is a gasket member provided separately from and movably attached to the exterior part so as to be movable in relation to, in an axial direction of, the valve member, the gasket member laterally surrounding the first and/or the second chamber so that when a vacuum pressure is exerted on the suction outlet in the first and/or the second position, the vacuum pressure causes the gasket member to move in the direction towards the suction outlet.

2. The medical sampling device of claim 1, further configured so that when a vacuum pressure from the vacuum source is exerted on the second chamber in the first position and on the first or the second chamber in the second position, the vacuum pressure pulls at least a part of the valve member towards the suction outlet.

3. The medical sampling device of claim 1, wherein each of the first and the second chambers comprises at least one top opening providing said fluid communication between the respective inlets and outlets in the first and the second positions of the valve member via the respective first and second chambers, a bottom surface positioned oppositely from the top opening, and lateral surfaces surrounding and connected to the bottom surface, the bottom and the lateral surfaces establishing internal surfaces of the respective chamber, and wherein the lateral surfaces and/or the bottom surface are provided as parts of the gasket member.

4. The medical sampling device of claim 1, wherein the valve housing comprises a seal surface, and wherein the gasket member comprises a lip extending at least partly between and/or being compressed between the exterior part and the seal surface.

5. The medical sampling device of claim 1, wherein the valve member is rotatable about an axis defining an axial direction, wherein the valve housing comprises a valve housing surface extending substantially radially in relation to the axial direction, and wherein the valve housing surface comprises at least one of a first valve port connected to the suction inlet, a second valve port connected to the sampling outlet, a third valve port connected to the suction outlet, or a fourth valve port connected to the sampling inlet.

6. The medical sampling device of claim 1, wherein the medical sampling device is adapted to be fixated to the medical device when connected to the suction connector thereof.

7. The medical sampling device of claim 1, wherein the medical sampling device comprises a moveable locking member configured to fixate the medical sampling device to an endoscope when the medical sampling device is connected to the suction connector.

8. The medical sampling device of claim 7, wherein the locking member comprises a locking support adapted to slide into engagement with a circumferentially extending barb of the suction connector.

9. A method of assembly of a medical sampling device, the method comprising:

providing a valve member having a first chamber and a second chamber;

providing a valve housing having a suction inlet, a suction outlet, a sampling outlet, a sampling inlet, and a valve member spacing; and attaching the valve member in the valve member spacing of the valve housing so as to be rotatable in relation to the valve housing between a first position and a second position, so that the first chamber in the first position establishes fluid communication between the suction inlet and the sampling inlet, the second chamber in the first position establishes fluid communication between the sampling outlet and the suction outlet, and the first chamber or the second chamber in the second position establishes fluid communication between the suction inlet and the suction outlet, wherein the valve member comprises an exterior part and an interior part, and the interior part is a gasket member provided separately from and movably attached to the exterior part so as to be movable in relation to, in an axial direction of, the valve member, the gasket member laterally surrounding the first and/or the second chamber so that when a vacuum pressure is exerted on the suction outlet in the first and/or the second position, the vacuum pressure causes the gasket member to move in the direction towards the suction outlet.

10. The method of claim 9, further comprising attaching a rotary knob to the valve housing and/or the valve member so that the valve member may be rotated between the first position and the second position by rotating the rotary knob.

11. A medical sampling system comprising:

a medical device having a suction channel and a suction connector in fluid communication with the suction channel; and a medical sampling device including:

a suction inlet adapted to be connected to the suction connector;

a suction outlet adapted to be connected to a vacuum source;

a sampling inlet adapted to be connected to a sample container;

a sampling outlet adapted to be connected to the sample container; and a valve having a valve member and a valve housing, wherein the valve member has a first and a second chamber and is rotatable in relation to the valve housing between a first and a second position, wherein in the first position, the first chamber establishes fluid communication between the suction inlet and the sampling inlet and the second chamber establishes fluid communication between the sampling outlet and the suction outlet, wherein in the second position, one of the first and the second chamber establishes fluid communication between the suction inlet and the suction outlet, and wherein the valve member comprises an exterior part and an interior part, and the interior part is a gasket member provided separately from and movably attached to the exterior part so as to be movable in relation to, in an axial direction of, the valve member, the gasket member laterally surrounding the first and/or the second chamber so that when a vacuum pressure is exerted on the suction outlet in the first and/or the second position, the vacuum pressure causes the gasket member to move in the direction towards the suction outlet.

12. The medical sampling system of claim 11, wherein the medical sampling device is attached to the medical device, and wherein the suction inlet of the medical sampling device is connected to the suction connector.

13. The medical sampling system of claim 11, further comprising the sample container, wherein the medical sampling device is attached to the sample container, and wherein the sampling inlet and the sampling outlet are connected to the sample container.

14. The medical sampling system of claim 11, wherein the medical device is an endoscope or a catheter.

15. The medical sampling system of claim 11, wherein the medical sampling device is packaged as a kit with at least one of the medical device or a sample container.

16. The medical sampling system of claim 15, wherein the medical sampling device is detached from the at least one of the medical device or the sample container.

17. The medical sampling system of claim 11, wherein each of the first and the second chambers comprises at least one top opening providing said fluid communication between the respective inlets and outlets in the first and the second positions of the valve member via the respective first and second chambers, a bottom surface positioned oppositely from the top opening, and lateral surfaces surrounding and connected to the bottom surface, the bottom and the lateral surfaces establishing internal surfaces of the respective chamber, and wherein the lateral surfaces and/or the bottom surface are provided as parts of the gasket member.

18. The medical sampling system of claim 11, wherein the valve housing comprises a seal surface, and wherein the gasket member comprises a lip extending at least partly between and/or being compressed between the exterior part and the seal surface.

* * * * *